US012742792B2

(12) United States Patent
Otvos et al.

(10) Patent No.: US 12,742,792 B2
(45) Date of Patent: Sep. 22, 2026

(54) METHODS AND SYSTEMS TO DETECT AND QUANTIFY THE AMOUNT OF LP-X AND OTHER ABNORMAL LIPOPROTEINS IN A BIOSAMPLE USING NMR SPECTROSCOPY

(71) Applicants: LipoScience, Inc., Morrisville, NC (US); National Institutes of Health, Bethesda, MD (US)

(72) Inventors: James D. Otvos, Apex, NC (US); Irina Shalaurova, Cary, NC (US); Alan Remaley, Bethesda, MD (US); Maureen Sampson, Silver Spring, MD (US); Lita Freeman, Bethesda, MD (US)

(73) Assignee: Laboratory Corporation of America Holdings, Burlington, NC (US)

( * ) Notice: Subject to any disclaimer, the term of this patent is extended or adjusted under 35 U.S.C. 154(b) by 872 days.

(21) Appl. No.: 17/947,738

(22) Filed: Sep. 19, 2022

(65) Prior Publication Data

US 2023/0024795 A1 Jan. 26, 2023

Related U.S. Application Data

(63) Continuation of application No. 16/188,435, filed on Nov. 13, 2018, now Pat. No. 11,467,171.

(60) Provisional application No. 62/589,113, filed on Nov. 21, 2017, provisional application No. 62/584,536, filed on Nov. 10, 2017.

(51) Int. Cl.

| | |
|---|---|
| ***G01N 33/92*** | (2006.01) |
| ***G01N 24/00*** | (2006.01) |
| ***G01N 35/00*** | (2006.01) |

(52) U.S. Cl.
CPC ............ *G01N 33/92* (2013.01); *G01N 24/00* (2013.01); *G01N 35/00693* (2013.01); *G01N 2035/00702* (2013.01); *G01N 2800/52* (2013.01)

(58) Field of Classification Search
CPC .. G01N 33/92; G01N 24/00; G01N 35/00693; G01N 2035/00702; G01N 2800/52
See application file for complete search history.

(56) References Cited

U.S. PATENT DOCUMENTS

| | | | |
|---|---|---|---|
| 4,933,844 | A | 6/1990 | Otvos |
| 5,343,389 | A | 8/1994 | Otvos |
| 6,617,167 | B2 | 9/2003 | Otvos et al. |

(Continued)

FOREIGN PATENT DOCUMENTS

| | | |
|---|---|---|
| EP | 0361214 | 4/1990 |

OTHER PUBLICATIONS

Aru, V. et al., "Quantification of lipoprotein profiles by nuclear magnetic resonance spectroscopy and multivariate data analysis," Trends Anal. Chem. 94:210-219 (2017).

(Continued)

*Primary Examiner* — Catherine T. Rastovski
*Assistant Examiner* — Nyla Gavia
(74) *Attorney, Agent, or Firm* — Kilpatrick Townsend & Stockton LLP

(57) ABSTRACT

Described herein are methods and systems for the determination of constituents in biosamples by NMR spectroscopy and more specifically for the determination of lipoprotein constituents LP-X, LP-Y, and LP-Z in blood plasma and serum.

19 Claims, 18 Drawing Sheets

(56) References Cited

U.S. PATENT DOCUMENTS

| | | | | |
|---|---|---|---|---|
| 7,243,030 B2 * | 7/2007 | Reeve | G01N 24/08 702/19 |
| 8,013,602 B2 * | 9/2011 | Otvos | G01R 33/307 324/309 |
| 2013/0328561 A1 * | 12/2013 | Otvos | G01R 33/4625 324/309 |
| 2017/0003269 A1 * | 1/2017 | Otvos | G16H 50/30 |

OTHER PUBLICATIONS

Freeman et al., "The Effects of MEDI6012 on Lipoproteins in Familial LCAT Deficiency Patients and a New NMR Method for Quantifying Lipoprotein-X", Circulation, vol. 136, No. 1, Nov. 14, 2017, pp. A16097-A16097.

Heimerl et al., "Lipid Profiling of Lipoprotein X: Implications for Dyslipidemia in Cholestasis", Biochimica Et Biophysica Acta—Molecular and Cell Biology of Lipids, vol. 1861, No. 8, Aug. 1, 2016, pp. 681-687.

Kostner GM., "Investigation of the Abnormal Low-Density Lipoproteins Occurring Patients with Obstructive Jaundice", The Biochemical Journal, vol. 157, No. 2, 1976, pp. 401-407.

Lawson et al., Solving Least Squares Problems, Englewood Cliffs, N.J., Prentice-Hall, 1974.

Narayanan S., "Biochemistry and Clinical Relevance of Lipoprotein X", Annals of Clinical and Laboratory Science, vol. 14, No. 5, 1984, pp. 371-374.

Neufeld et al., "Lipoprotein X Causes Renal Disease in LCAT Deficiency", Arteriosclerosis, Thrombosis, and Vascular Biology. Poster Abstract Presentations Session Title: Poster Session I, vol. 36, No. 1, May 1, 2016, pp. 1-5.

Otvos et al., "Relationships between the Proton Nuclear Magnetic Resonance Properties of Plasma Lipoproteins and Cancer", Clin. Chem., vol. 37, No. 3, 1991, pp. 369-376.

Parmar, Y. et al., "Detection of vesicular lipoproteins in lecithin:cholesterol acyltransferase-deficient plasma by H-NMR spectroscopy," J. Lipid Res. 30:765-771 (1989).

PCT/US2018/060597 , "International Search Report and Written Opinion", Feb. 1, 2019, 13 pages.

Shamburek et al., "Familial Lecithin: Cholesterol Acyltransferase Deficiency: First-in-Human Treatment with Enzyme Replacement", Journal of Clinical Lipidology, 2016, vol. 10, pp. 356-367.

Vaisman et al., "Reduction of LpX and Improvement in Kidney Function in LCAT-KO Mice by Enzyme Replacement Therapy", Arteriosclerosis, Thrombosis, and Vascular Biology. Poster Abstract Presentations Session Title: Poster Session I, vol. 36, No. 1, May 1, 2016, pp. 1-5.

* cited by examiner

High Bilirubin Patient

METHODS AND SYSTEMS TO DETECT AND QUANTIFY THE AMOUNT OF LP-X AND OTHER ABNORMAL LIPOPROTEINS IN A BIOSAMPLE USING NMR SPECTROSCOPY

PRIORITY

This application is a continuation of U.S. application Ser. No. 16/188,435, filed Nov. 13, 2018, which claims priority to U.S. Provisional Patent Application No. 62/584,536, filed Nov. 10, 2017, and U.S. Provisional Patent Application No. 62/589,113, filed Nov. 21, 2017, all of which are hereby incorporated by reference in their entireties herein.

FIELD

Described herein are methods and systems for the determination of constituents in blood plasma and serum and more specifically for the determination of lipoprotein constituents in blood plasma and serum.

BACKGROUND

Lipoprotein X (LP-X) is an abnormal lipoprotein that appears in the sera of patients with obstructive jaundice. LP-X is a spherical particle typically between about 30 and 70 nm in diameter. Its density is between 1.006 and 1.063 g/ml, which is in the same range as normal low density lipoproteins (LDL). Phospholipids (about 66 percent) and unesterified cholesterol (about 22 percent) make up the bulk of LP-X; also, protein, cholesterol esters and triglycerides comprise about 12 percent of LP-X. See Narayanan, Biochemistry and Clinical Relevance of Lipoprotein X, 14 Annals of Clinical and Laboratory Science 371 (1984).

LP-X is an abnormal lipoprotein that is relatively rare, appearing in only about 0.1 percent of the population. Its presence can be very difficult to discern with standard cholesterol screening techniques; instead, it is typically identified through electrophoresis procedures, which are relatively laborious and provide results that are difficult to quantify. Other abnormal lipoproteins include LP-Y and LP-Z that often coexist with LP-X or are also found in patients with liver disease or lecithin-cholesterol acyltransferase (LCAT) deficiency.

Identification of LP-X and other abnormal lipoproteins can be quite important in the treatment of a patient. For example, a patient whose lipid profile indicates an elevated cholesterol level (to which LP-X may contribute) may be treated for cardiovascular disease risk with a cholesterol-lowering "statin" drug when in fact, the presence of LP-X may indicate that the patient is actually suffering from, e.g., liver disease or LCAT deficiency (not elevated LDL cholesterol), with the result that the aforementioned treatment may exacerbate, rather than address, the patient's condition. Therefore, it would be desirable to have a method of detecting LP-X and other abnormal lipoproteins that is easily administered and accurate. It would also be desirable to have a method of detecting LP-X and other abnormal lipoproteins that would dovetail with routine tests being performed on a patient. For example, patients with familial LCAT deficiency may be treated with infusions of recombinant LCAT to lower levels of LP-X (Shamburek et al., J Clin Lipidol. 2016:356-67).

Therefore, methods and systems are needed for assays that accurately determine LP-X and other abnormal lipoproteins in a plasma or serum sample. Described herein are new methods and systems to accurately detect and quantify the amount of LP-X and other abnormal lipoproteins in a biosample using NMR spectroscopy.

SUMMARY

Described herein are new methods and systems to accurately determine the presence and amount of LP-X in a biosample using NMR spectroscopy. The invention may be embodied in a variety of ways. In certain embodiments, methods and systems include determination of LP-X in a subject or patient. In some embodiments, methods determine a patient's response to therapy.

In some embodiments, a method of diagnosing a subject for the presence of LP-X comprises the steps of acquiring an NMR spectrum of a blood plasma or serum sample obtained from the subject and determining the presence of LP-X in the sample based on the deconvolved NMR spectrum of the sample. In certain embodiments, a deconvolution model is applied to the spectrum to account for the presence of LP-X and other abnormal lipoproteins, e.g., LP-Y and/or LP-Z.

In some embodiments, methods described herein include steps of identifying the presence of LP-X or LP-Z on the basis of "bad fit" or mismatch between measured and calculated plasma signals using a standard deconvolution model. In some embodiments, the identification of bad fit using a standard deconvolution model prompts application of a modified deconvolution model that includes LP-X, LP-Y, and/or LP-Z, so as to properly quantify the amount of LP-X and these other abnormal lipoproteins.

In certain embodiments, a method of evaluating a patient's response to a therapy comprises obtaining a first biosample from the patient at a first time point, obtaining a second biosample from the patient at a second time point, where the first time point is before the second time point, measuring the patient's LP-X concentration in the first and the second biosamples, determining the patient is responsive to the therapy if the concentration of LP-X in the second biosample is lower than the concentration of LP-X in the first biosample, where the measuring LP-X is by determining the presence of LP-X in the sample based on deconvolution of the NMR spectrum of the sample. In certain embodiments, the deconvolution of the NMR spectrum may further include LP-Y and/or LP-Z.

In some embodiments, a system for screening a subject for the presence of LP-X comprises an NMR spectrometer for programmably acquiring a measured lipid signal lineshape of an NMR spectrum of a biosample; a computer program means for storing the measured lineshape of the sample; a computer program means for storing reference spectra for each of a plurality of lipoprotein constituents, where one or more of the constituents comprise LP-X and optionally LP-Y and/or LP-Z; a computer program means for calculating a deconvolved lineshape based on the derived concentrations of the lipoprotein constituents of the biosample and the reference spectra; and a computer program means for comparing the measured lipid signal lineshape and the calculated lineshape to determine the degree of correlation between the calculated lineshape and the measured lipid signal lineshape. In some embodiments, the degree of correlation can be determined by the quantification of the residual.

In some embodiments, a system configured to determine the concentrations of LP-X in patient biosamples comprises one or more processors configured to (a) obtain and analyze NMR signal spectra of the biosamples, wherein the NMR signal spectra comprises a LP-X methyl proton signal at a first region, and optionally a LP-Y methyl proton signal at a second region and a LP-Z methyl proton signal at a third region; (b) deconvolve signal data associated with the LP-X and optionally the LP-Y and/or LP-Z signals; and (c) compare data from the deconvolved signal data with a priori calibration data corresponding to standard samples with known concentrations of LP-X and optionally LP-Y and LP-Z to determine the concentrations of LP-X in the biosample.

Yet other embodiments are directed to NMR analyzers. The NMR analyzer may include a NMR spectrometer, a flow probe in communication with the spectrometer, and a controller in communication with the spectrometer configured to obtain NMR signal of a defined single peak region of NMR spectra associated with LP-X of a fluid specimen in the flow probe and generate a patient report providing a LP-X level.

The controller can include or be in communication with at least one local or remote processor, wherein the at least one processor is configured to: (i) obtain a composite NMR spectrum of a fitting region of an in vitro plasma or serum biosample; and (ii) deconvolve the composite NMR spectrum using a defined deconvolution model to generate the LP-X level. In certain embodiments, the deconvolution model comprises at least one of high density lipoprotein (HDL) components, low density lipoprotein (LDL) components, VLDL (very low density lipoprotein)/chylomicron components, and/or LP-Y and LP-Z.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

BRIEF DESCRIPTION OF FIGURES

The present disclosure may be better understood with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Further, the flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

DETAILED DESCRIPTION

Figure 1:
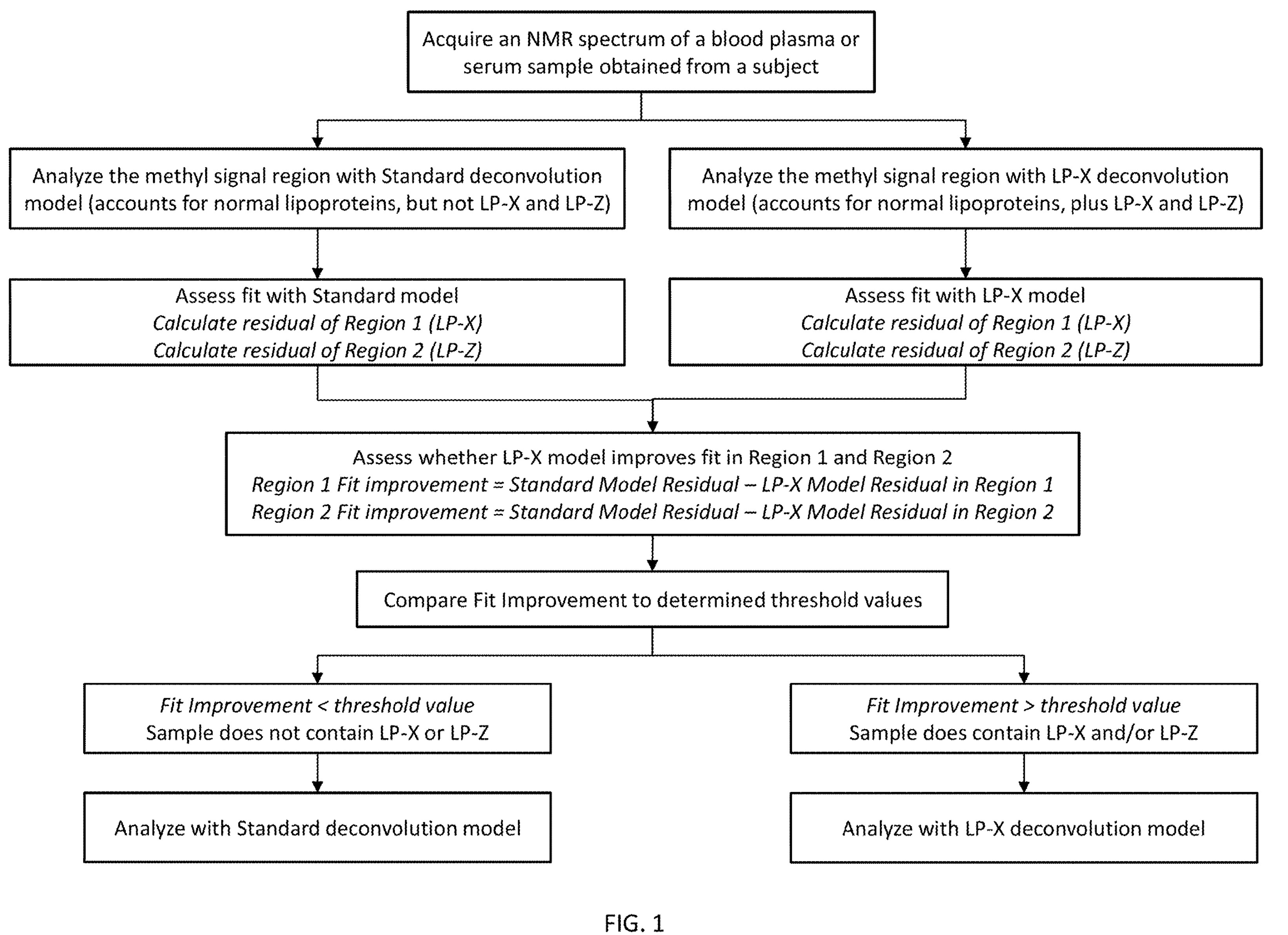
FIG. 1 shows a schematic of a method to screen for LP-X and other abnormal lipoproteins according to embodiments of the present invention.

LP-X is an abnormal lamellar vesicular particle enriched in phospholipids and unesterified cholesterol, and has been determined to be nephrotoxic. Traditionally, LP-X levels have been determined by agarose gel electrophoresis based on the reverse migration of LP-X towards the cathode. The present disclosure describes the use of nuclear magnetic resonance (NMR) spectroscopy to identify and quantify LP-X. Such measurements may be used in patients in whom LP-X accumulates, such as those patients with alcoholic hepatitis, obstructive jaundice, or familial LCAT deficiency, so as to determine risk of adverse clinical outcomes and/or indicate need for appropriate therapies. Further, some patients may have variable amounts of a triglyceride-rich lipoprotein referred to as LP-Y and an abnormal, highly triglyceride-enriched low-density lipoprotein (LDL) particle known as LP-Z, both of which are also quantifiable by NMR. The species referred to as LP-Z herein has previously been described as "highly triglyceride enriched LDL" (Kostner G M et al., Biochem J. 1976; 157:401-407.).

Terms and Definitions

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about V." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail fir brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input. The term "about" refers to +/−10% (mean or average) of a specified value or number.

The term "biosample" refers to in vitro blood, plasma, serum, CSF, saliva, lavage, sputum, urine, or tissue samples of humans or animals. Embodiments of the invention may be particularly suitable for evaluating human blood plasma or serum biosamples. The blood plasma or serum samples may be fasting or non-fasting.

The term "patient" or "subject" is used broadly and refers to an individual that provides a biosample for testing or analysis.

The term "clinical disease state" means an at-risk medical condition that may indicate medical intervention, therapy, therapy adjustment or exclusion of a certain therapy (e.g., pharmaceutical drug) and/or monitoring is appropriate. Identification of a likelihood of a clinical disease state can allow a clinician to treat, delay or inhibit onset of the condition accordingly. Examples of clinical disease states include, but are not limited to, CHD, CVD, stroke, type 2 diabetes, prediabetes, dementia, Alzheimer's, cancer, arthritis, rheumatoid arthritis (RA), kidney disease, liver disease, pulmonary disease, COPD (chronic obstructive pulmonary disease), peripheral vascular disease, congestive heart failure, organ transplant response, and/or medical conditions associated with immune deficiency, abnormalities in biological functions in protein sorting, immune and receptor recognition, inflammation, pathogenicity, metastasis and other cellular processes.

Methods to Measure LP-X and Other Abnormal Lipoproteins

Described herein are novel methods (i.e., assays) utilizing NMR to characterize LP-X, LP-Y, and LP-Z in a biological sample. The methods may be embodied in a variety of ways.

For example, in certain aspects, the methods may be used to determine whether treatment with a therapy is warranted for a subject (i.e., patient). Thus, in some embodiments, the assays utilize NMR to characterize the effects of a therapy on LP-X in patient plasma samples. Quantification of LP-X by NMR spectroscopy can be compared to LP-X measured semi-quantitatively by traditional agarose gel electrophoresis.

As noted above, most individuals (i.e. "normal" healthy subjects) have very low levels or no LP-X or LP-Z. In contrast, variable amounts of LP-Y are found in both healthy and diseased individuals. In subjects exhibiting the presence of LP-X or LP-Z, such as subjects having obstructive jaundice or alcoholic hepatitis, LP-X levels may be elevated to varying degrees. Methyl lipid signals from LP-X, LP-Y, and LP-Z each have a unique spectral shape and position in NMR spectroscopy, different from those of 'normal' lipoprotein particles. The assays described herein utilize these unique spectral lineshapes to detect and quantify LP-X, LP-Y, and LP-Z in a serum or plasma sample.

In many instances, the method begins with a conventional NMR lipoprotein screening in which a calculated plasma lineshape is generated based on derived concentrations of lipoprotein components in the sample, with no LP-X or LP-Z signal representation in the deconvolution model (the usual deconvolution model does, however, include LP-Y). In such instances, a determination that the expected degree of agreement or correlation between the measured and calculated plasma signals is less that a predetermined number will indicate the possible presence of LP-X and/or LP-Z.

FIG. 1 shows a schematic of a method to screen for LP-X. Thus, one aspect of the disclosure is directed to a method of screening a subject for the presence of LP-X and/or LP-Z. The method may comprise the initial step of producing a nuclear magnetic resonance (NMR) methyl lipid signal lineshape of a blood plasma or serum sample obtained from a subject. Next, calculated lineshapes can be generated for the sample, the lineshapes being based on deconvolution-derived concentrations of lipoprotein components potentially present in the sample (the derived concentration of each of the lipoprotein components being the function of a reference spectrum for that component and a calculated reference coefficient). The deconvolution model can include standard lipoprotein reference spectra, without including reference spectra for LP-X or LP-Z components, and a LP-X deconvolution model which in addition to the standard lipoprotein reference spectra also includes those for one (or more) abnormal lipoprotein components, such as LP-X and LP-Z. The residual or degree of fit to the model can be calculated for particular spectral regions and a Region Fit Improvement value can be calculated. If the Region Fit Improvement Value is less than the determined threshold value, then the sample is determined to not contain LP-X and/or LP-Z, and the standard deconvolution model can be utilized for further analysis of the biosample. Conversely, if the Region Fit Improvement Value is greater than the determined threshold value, then the sample is determined to contain some amounts of LP-X and/or LP-Z, and the LP-X deconvolution model can be utilized for further analysis of the biosample instead of the standard deconvolution model.

Figure 2:
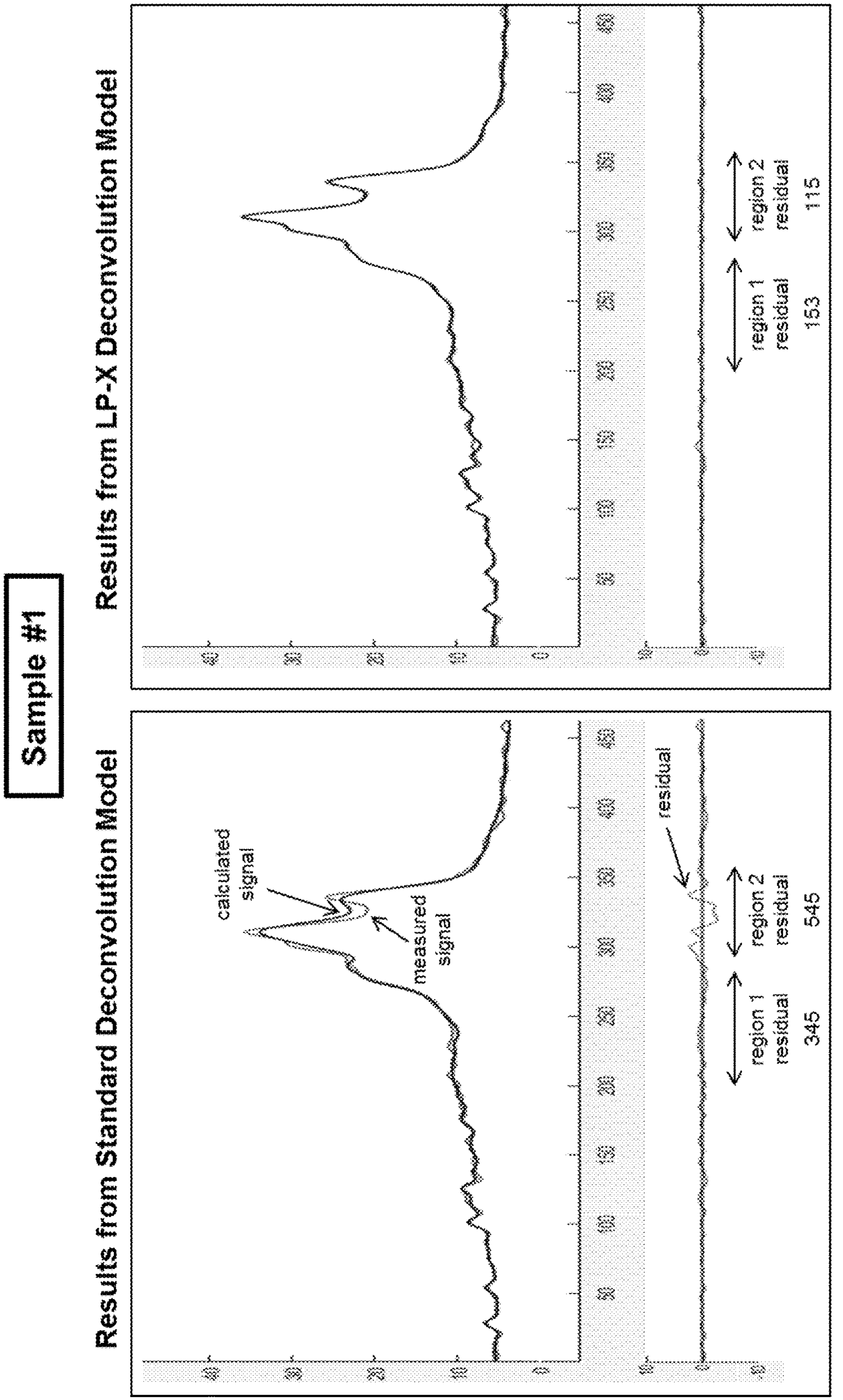
FIG. 2 shows fit results from the standard deconvolution model and LP-X deconvolution model with a poor fit and large residual signal according to embodiments of the present invention.
Figure 3:
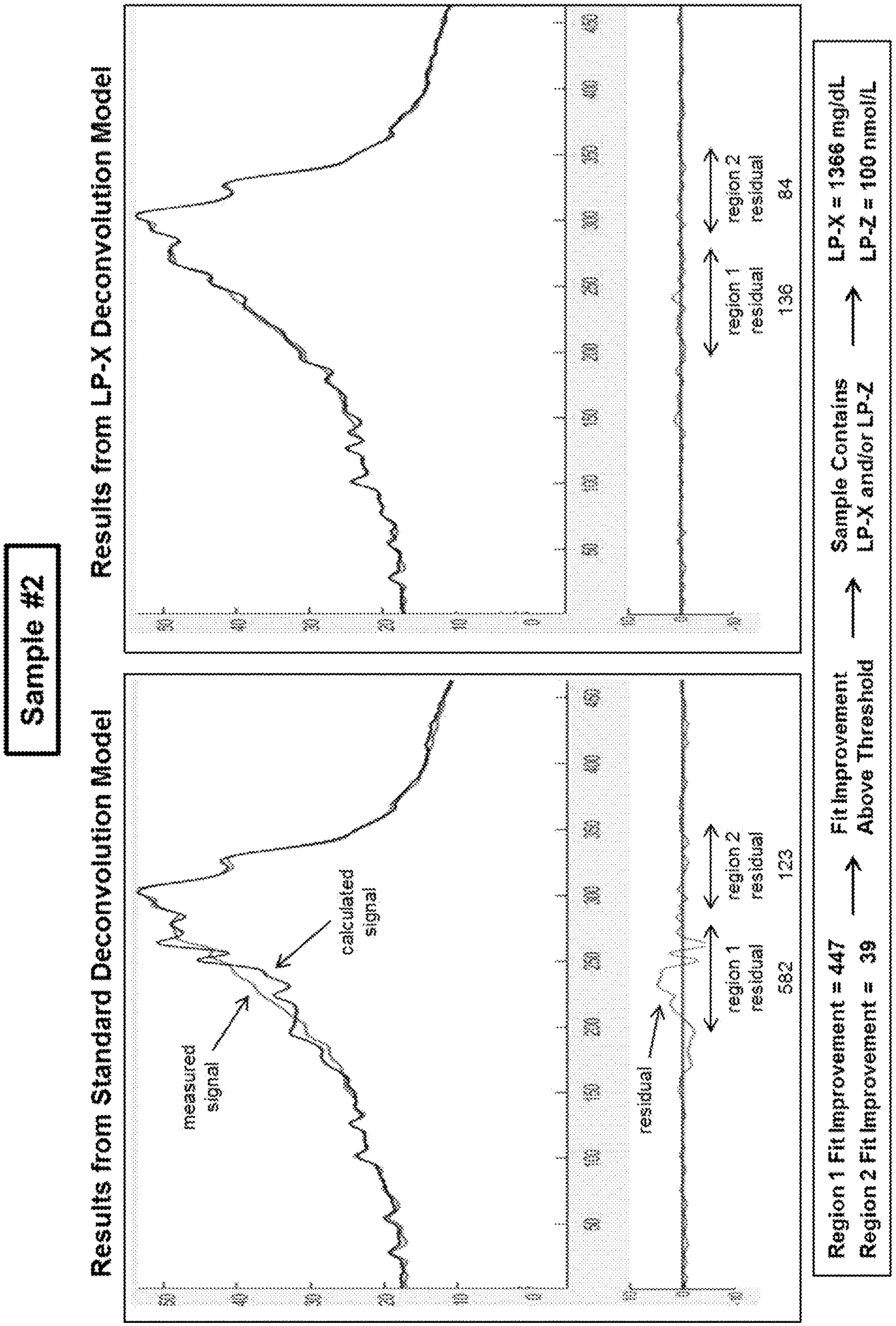
FIG. 3 shows fit results from the standard deconvolution model and LP-X deconvolution model with a poor fit and large residual signal mainly in the LP-Z region (Region 2) according to embodiments of the present invention.
Figure 4:
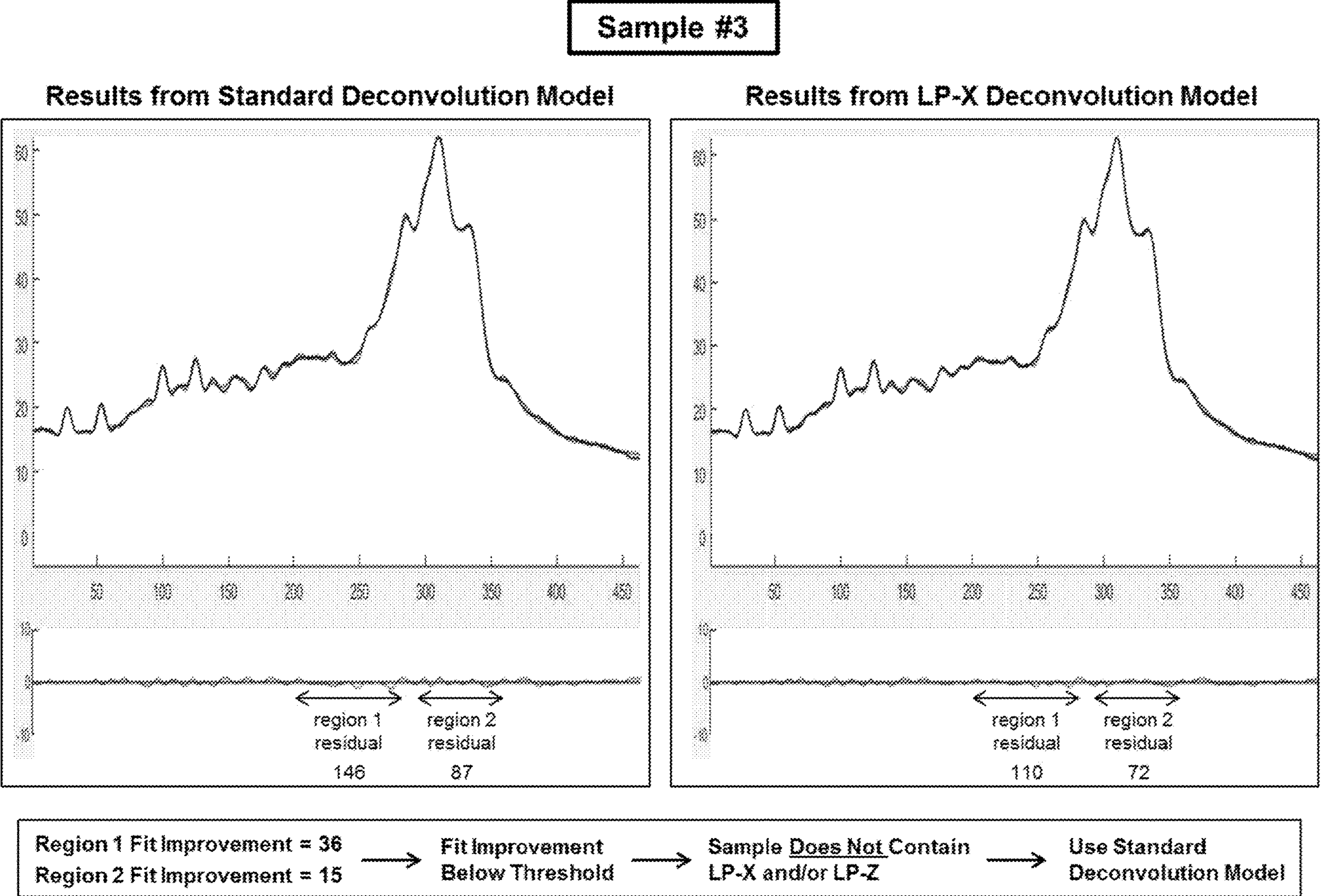
FIG. 4 shows fit results from the standard deconvolution model and LP-X deconvolution model with a good fit and small residual signal mainly in the LP-X region (Region 1) according to embodiments of the present invention.

FIGS. 2-4 are examples of the LP-X screening process. In FIG. 2, calculated lineshapes were generated using both the standard and LP-X models and the residual values for Region 1 and Region 2 of each model were calculated. These residual values were used to calculate Region Fit Improvement Values of 192 and 430, the latter being greater than the threshold value of 80 for Region 2 Fit Improvement. The screening process used in the biosample of FIG. 2 determined that LP-X and/or LP-Z was present in the biosample and that the LP-X deconvolution model should be used for additional analysis performed on the sample. Subsequent analysis of biosample #1 showed that the concentration of LP-X in the sample was 157 mg/dL and the concentration of LP-Z was 3368 nmol/L. The same process was utilized to screen biosamples shown in FIGS. 3 and 4. The screening process used in the biosample of FIG. 3 determined that LP-X and/or LP-Z was present in the biosample and that the LP-X deconvolution model should be used for additional analysis performed on the sample. Subsequent analysis of biosample #2 showed that the concentration of LP-X in the sample was 1366 mg/dL and the concentration of LP-Z was 100 nmol/L. The screening process used in the biosample of FIG. 4 determined that LP-X and LP-Z were not present in the biosample and that the standard deconvolution model should be used for additional analysis performed on the sample. This method can enable the practitioner, during a routine and easily-conducted cholesterol screening, to be alerted to the presence of LP-X or LP-Z in a subject and begin diagnosis and treatment of conditions associated with these abnormal lipoproteins or to prevent a subject from receiving medications for cholesterol management which may be deleterious.

Figure 5:
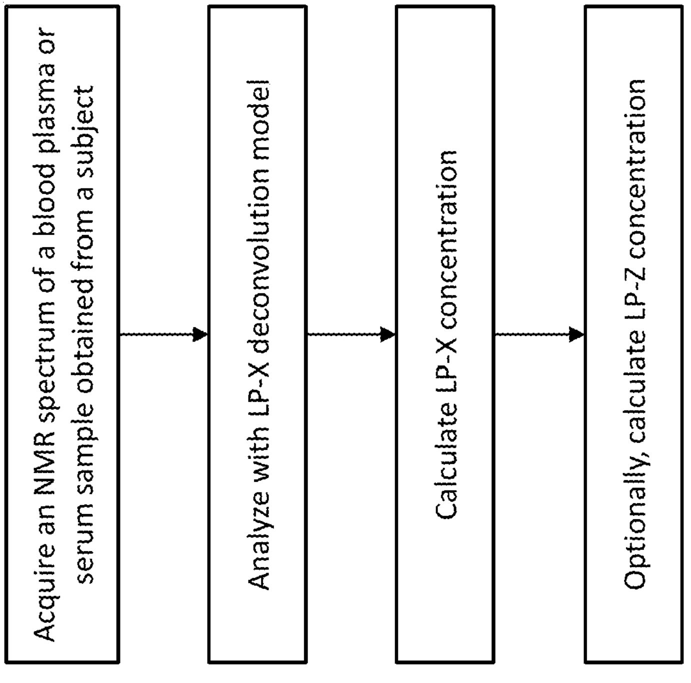
FIG. 5 shows a schematic of a method to quantify LP-X and/or LP-Z according to embodiments of the present invention.

FIG. 5 shows a schematic of a method to calculate a concentration of lipoprotein X and/or LP-Z. The concentration of LP-X, LP-Z, and ratio of LP-Z to total LDL particles (LDLP) can be determined.

NMR spectroscopy has been used to concurrently measure very low density lipoprotein (VLDL), low density lipoprotein (LDL) and high density lipoprotein (HDL) particle subclasses from in vitro blood plasma or serum samples. See, U.S. Pat. Nos. 4,933,844 and 6,617,167, the contents of which are hereby incorporated by reference as if recited in full herein. Generally stated, to evaluate the lipoproteins in a blood plasma and/or serum sample, the amplitudes of a plurality of NMR spectroscopy derived signals within a chemical shift region of NMR spectra are derived by deconvolution of the composite methyl signal envelope to yield subclass concentrations. The subclasses are represented by many (typically over 60) discrete contributing subclass signals associated with NMR frequency and lipoprotein diameter. The NMR evaluations can decompose the measured plasma NMR signals to produce concentrations of different lipoprotein subpopulations, for VLDL, LDL and HDL. These sub-populations can be further characterized as associated with a particular size range within the VLDL, LDL or HDL subclasses.

In the past, an "advanced" lipoprotein test panel, such as the NMR LIPOPROFILE® lipoprotein test, available from LapCorp, Burlington, N.C., has typically included a total HDL particle (HDL-P) measurement that sums the concentration of all the HDL subclasses and a total LDL particle (LDL-P) measurement that sums the concentration of all the LDL subclasses. The LDL-P and HDL-P numbers represent the concentration of those respective particles in concentration units such as nmol/L.

Figure 6:
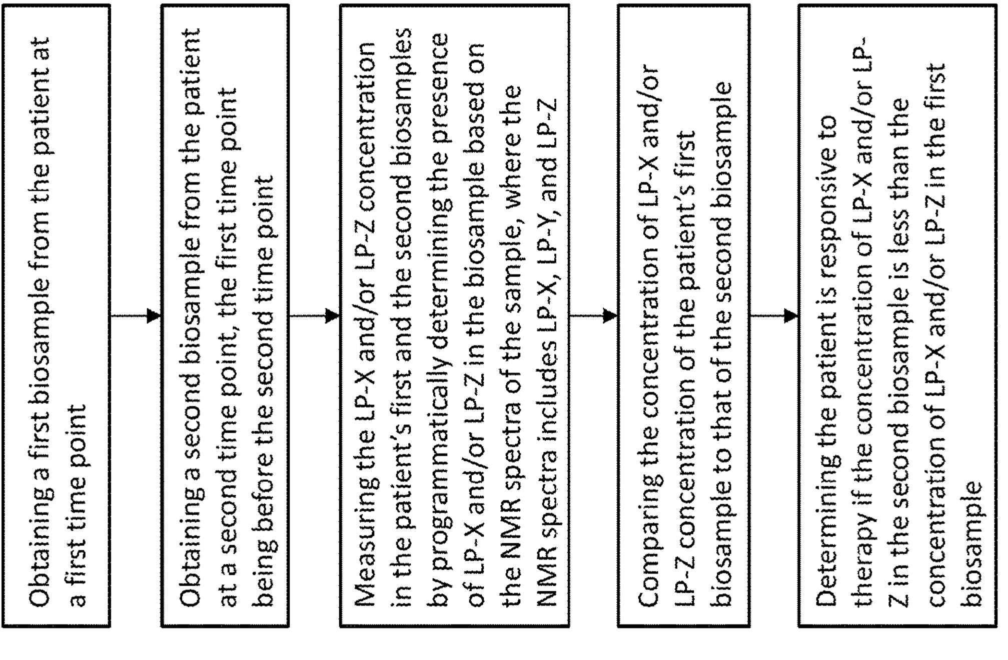
FIG. 6 shows a schematic of a method to use LP-X measurement.

FIG. 6 shows an embodiment of a method of evaluating a patient's response to therapy. For example, in an embodiment of the method, a (measured) composite plasma methyl signal envelope within the complete NMR spectrum of a biosample (e.g., blood plasma or serum) is obtained. The NMR composite signal envelope is computationally decomposed using a defined deconvolution model that includes reference signals of all of the HDL, LDL, and VLDL subspecies normally found in human plasma, plus at least one reference signal for LP-X centered at a defined chemical shift location (e.g., 0.97 ppm). The derived LP-X concentration can be expressed in terms of NMR signal area, or converted into other units (for example, mg/dL cholesterol mass concentration units) with the use of an appropriate conversion factor(s).

In some embodiments, a method of diagnosing a subject for the presence of LP-X and/or LP-Z comprises the steps of acquiring an NMR spectrum of a blood plasma or serum sample obtained from the subject and programmatically determining the presence/amount of LP-X in the sample based on the deconvolved NMR spectrum of the sample. In an embodiment, the deconvolution model includes representatives of the multiple VLDL (sometimes referred to as TRL, standing for triglyceride-rich lipoproteins), LDL, and HDL subclasses plus that of LP-X. Additionally or alternatively, the deconvolution model may comprise representatives of LP-Y and LP-Z. In some embodiments, the acquiring step of the method comprises (a) producing a measured lipid signal lineshape from an NMR spectrum of a blood plasma or serum sample obtained from a subject; and (b) generating a calculated lineshape for the sample, the calculated lineshape being based on derived concentrations of lipoprotein components potentially present in the sample, wherein lipoprotein components include LP-X, the derived concentration of each of the lipoprotein components being the function of a reference spectrum for that component and a calculated reference coefficient, wherein one of the lipoprotein components for which a concentration is calculated is LP-X. In an embodiment, the concentrations of other components such as, but not limited to, LP-Y and LP-Z are derived. In some embodiments, the method further comprises (c) determining that the degree of correlation between the calculated plasma signal lineshape and the measured plasma signal lineshape for the sample; and (d) determining the presence of LP-X based on the calculated lineshape if the degree of disagreement between the calculated lineshape and the measured lineshape (also called the "residual") for the sample is above a predetermined threshold. In some embodiments, step (b) of the method comprises calculating the reference coefficients for the calculated lineshape based on a linear least squares fit technique.

In some embodiments, the NMR spectrum of the sample includes an LP-X methyl proton signal in a first region, LP-Y methyl proton signal in a second region, and LP-Z methyl proton signal in a third region. In some embodiments, the first region is centered at 0.97±0.01 ppm, the second region is centered at 0.78±0.01 ppm, and the third region is centered at 0.77±0.01 ppm. In some embodiments, the NMR spectrum further includes methyl proton signals from one or more subspecies of LDL, HDL, and VLDL lipoproteins.

In certain embodiments, the method further comprises deconvolving signal data associated with the LP-X, LP-Y, and LP-Z methyl signals; and comparing data from the deconvolved signal data with a priori calibration data corresponding to standard samples with known concentrations of LP-X, LP-Y, and LP-Z to determine the concentrations of LP-X in the sample. In some embodiments, the method further comprises determining the presence of LP-X, LP-Y, and/or LP-Z in the sample. In some embodiments, the method further comprises determining the concentration of LP-X, LP-Y and/or LP-Z in the sample. The plasma NMR signal envelope includes peaks that align with LP-X, LP-Y, and LP-Z, respectively. The presence of LP-X can be detected using the difference between total sample signal as given by the total peak area of the sample signal and those portions of the signal from branched-chain amino acids, protein, TRL, HDL, and LDL. In some embodiments where a sample includes LP-X, analysis of the NMR spectrum derived from the sample using a "standard" deconvolution model exhibits a "bad fit" which can prompt the use of a modified deconvolution model to measure the concentration of LP-X. In some embodiments the application of such a modified deconvolution model results in a "good fit" between the measured and calculated lineshapes.

Stated differently, while not being bound to any particular theory, in some embodiments, the measured LP-X signal at 0.97±0.01 ppm can be referred to as LP-X.

The lineshape deconvolution can be achieved with a non-negative least squares fitting program (Lawson, C T, Hanson R J, Solving Least Squares Problems, Englewood Cliffs, N.J., Prentice-Hall, 1974). This avoids the use of negative concentrations which can lead to error especially in low signal to noise spectra. Mathematically, a suitable lineshape analysis is described in detail for lipoproteins in the paper by Otvos, J D, Jeyarajah, E J and Bennett, D W, Clin Chem, 37, 377, 1991. A synthetic baseline correction function may also be used to account for baseline offsets from residual protein components. This can take the form of a quadratic or other polynomial function. Weighting factors are determined and the fit can be optimized by minimizing the root mean squared deviation between the experimental and calculated spectrum. See, e.g., U.S. Pat. Nos. 4,933,844 and 6,617,167 for a description of deconvolving composite NMR spectra to measure subclasses of lipoproteins, the contents of which are hereby incorporated by reference as if recited in full herein. See also, U.S. Pat. No. 7,243,030 for a description of a protocol to deconvolve chemical constituents with overlapping signal contribution, the contents of which are hereby incorporated by reference as if recited in full herein.

In some embodiments, the sample can be blood, serum, plasma, cerebral spinal fluid, or urine. In some embodiments, the method further comprises the step of producing a report listing the concentrations of the lipoprotein constituents present in the sample. In certain embodiments, the method further comprises the step of identifying one of the conditions characterized by elevated LP-X levels (such as liver disease or LCAT deficiency) in the subject following the determining step.

In some embodiments, a method of evaluating a patient's response to a therapy comprises obtaining a first biosample from the patient at a first time point, obtaining a second biosample from the patient at a second time point, wherein the first time point is before the second time point, measuring the patient's LP-X concentration in the first and the second biosamples, determining the patient is responsive to the therapy if the concentration of LP-X in the second biosample is lower than the concentration of lipoprotein in the first biosample, wherein the measuring LP-X is by programmatically determining the presence of LP-X in the sample based on the NMR spectrum of the sample, wherein the NMR spectrum of the sample includes LP-X, LP-Y, and LP-Z.

Plasma samples containing LP-X and/or LP-Z can be identified by the quality control procedures employed for clinical lipoprotein particle analysis during, e.g., NMR Lipo-Profile testing on, e.g., a Vantera NMR clinical analyzer. Using a deconvolution model typical of normal lipoprotein distributions provides a "good fit" for normal (e.g., subjects who are healthy and do not have liver problems) subjects, but a "bad fit" for patients having LP-X, e.g., for subjects having liver disease (e.g., alcoholic hepatitis). This bad fit is due to the contribution of LP-X and in some cases also LP-Y and/or LP-Z. These samples are abnormal as LP-X and LP-Z have unique spectral shape (lineshape) and result in a "bad fit" or mismatch between measured and calculated plasma signals using a standard deconvolution model. This mismatch is because the unusual lineshapes of LP-X and LP-Z lipid methyl NMR signals are not accounted for in the standard model, resulting in a delta (i.e., "residual," see, e.g., FIG. 16) between the measured plasma signal and calculated plasma signal for a patient having LP-X, LP-Y, and/or LP-Z present, such as a patient with alcoholic hepatitis or other liver disease.

To quantify LP-X and LP-Z in arbitrary units of signal area, a modified deconvolution model has been developed using LP-X and LP-Z reference standards. LP-X (75% phosphatidylcholine, 25% cholesterol) may be synthetically derived and/or isolated from human serum samples subjected to chromatographic separation using methods known in the art. Similarly, LP-Z can be isolated by agarose gel filtration chromatography of plasma obtained from a human patient with LP-Z (e.g., typically a patient having liver disease such as alcoholic hepatitis or biliary cholestasis). The plasma of some animals may also be appropriate sources of LP-X, LP-Y, and/or LP-Z for use as standards. With these reference standards, a modified deconvolution model can be generated to deconvolve NMR spectra for LP-X and LP-Z.

Systems

Also disclosed herein are systems for screening a subject for the presence of LP-X and systems for quantifying LP-X in biosamples. In certain embodiments, a system for screening a subject for the presence of LP-X comprises an NMR spectrometer for acquiring a measured lipid signal lineshape of an NMR spectrum of a biosample; a computer program means for storing the measured lineshape of the sample; a computer program means for storing reference spectra for each of a plurality of lipoprotein constituents, one or more of the constituents being LP-X, LP-Y, and/or LP-Z; a computer program means for calculating a calculated lineshape based on the derived concentrations of the lipoprotein constituents of the biosample and the reference spectra; and a computer program means for comparing the lipid signal lineshape and the calculated lineshape to determine the degree of correlation between the calculated lineshape and the measured lineshape. In some embodiments, the computer program means for storing reference spectra comprise means for storing lipoproteins HDL, LDL, and/or VLDL. In certain embodiments, the system further comprises an output device for producing a report indicating the presence of LP-X and/or the concentration of LP-X.

In some embodiments, a system may be configured to determine the concentrations of LP-X in patient biosamples, the system comprising: one or more processors configured to (a) obtain and analyze NMR signal spectra of the biosamples, wherein the NMR signal spectra comprises LP-X methyl proton signal at a first region and (b) deconvolve signal data associated with the LP-X methyl proton signal; and (c) compare data from the deconvolved signal data with a priori calibration data corresponding to standard samples with known concentrations of LP-X to determine the concentrations of LP-X in the biosample. The system may further comprise components to obtain and analyze signals for a LP-Y methyl proton signal at a second region and a LP-Z methyl proton signal at a third region. In some embodiments, the first region is centered at 0.97±0.01 ppm, the second region is centered at 0.78 ppm±0.01, and the third region is centered at 0.77±0.01 ppm.

Also disclosed herein are computer programs for determining the concentration of LP-X in patient biosamples. In some embodiments, a computer program product may include computer readable program code that applies a conversion factor to generate the measurement of LP-X in μmol/L. In some embodiments, the computer program product can include computer readable program code that generates a patient report with the LP-X measurement. In some embodiments, the computer program code that provides the measurement can be configured to evaluate NMR spectra of an in vitro blood plasma or serum patient sample using NMR signal having a first region centered at 0.97±0.01 ppm, second region centered at 0.78 ppm±0.01, and third region centered at 0.77±0.01 ppm.

In certain embodiments, a computer program product may determine the concentrations of LP-X in patient biosamples, the computer program product comprising a non-transitory computer readable storage medium having computer readable program code embodied in the medium, the computer-readable program code comprising a computer readable program code that obtains NMR signal spectra and applies a deconvolution model comprising LP-X methyl proton signal at a first region, optionally a LP-Y methyl proton signal at a second region, and optionally a LP-Z methyl proton signal at a third region; and a computer readable program code that determines the concentrations of LP-X in the biosample. In some embodiments, the non-transitory computer readable storage medium further comprises computer readable program code for deconvolving signal data associated with the LP-X, LP-Y, and LP-Z signals.

Figure 7:
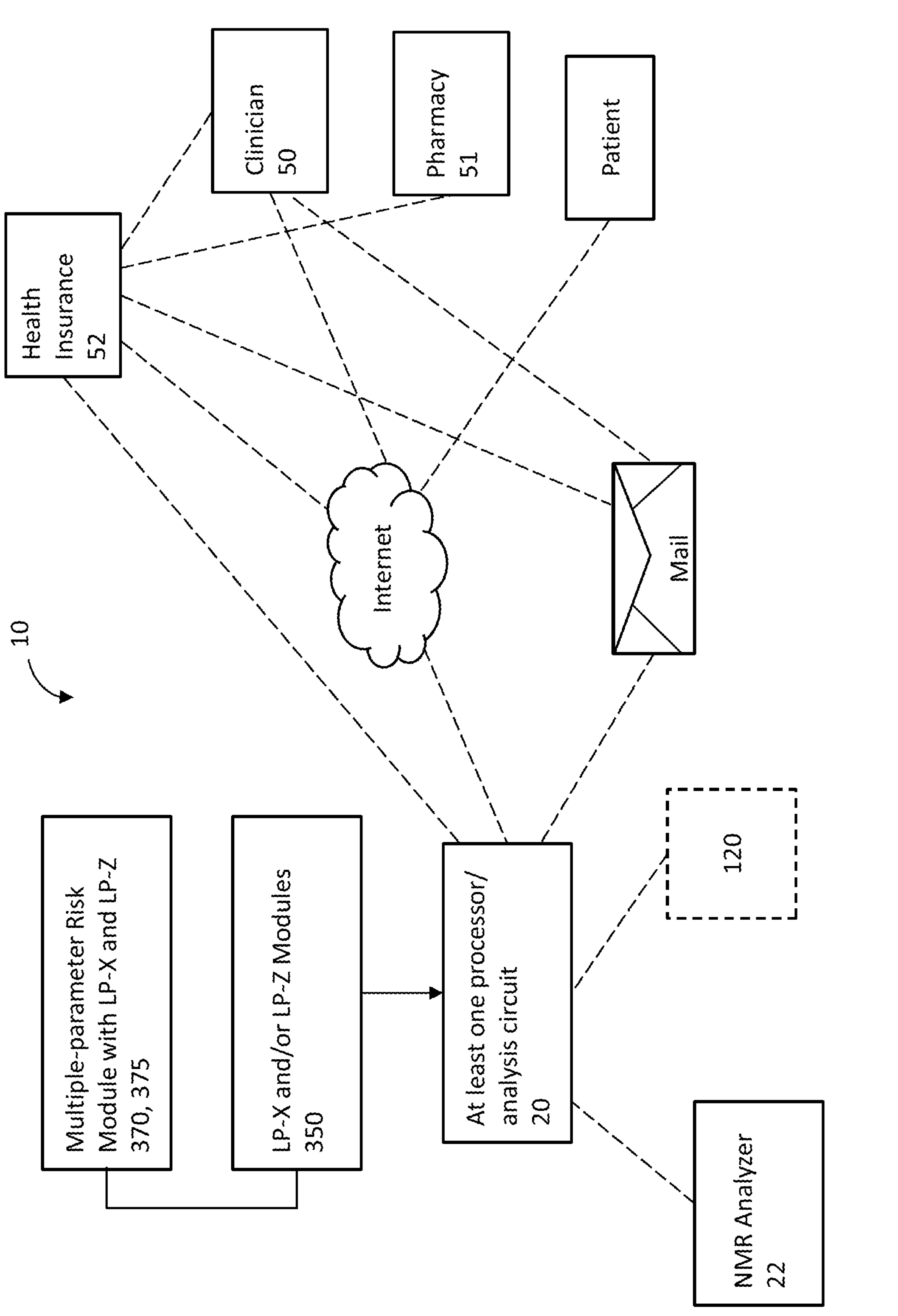
FIG. 7 shows s a schematic illustration of a system for LP-X evaluation module and/or circuit using according to embodiments of the present invention.

Referring now to FIG. 7, it is contemplated that the LP-X and/or LP-Z measurement analysis can be carried out using a system 10 with an NMR clinical analyzer 22 as described, for example, with respect to FIG. 8, below and/or in U.S. Pat. No. 8,013,602, the contents of which are hereby incorporated by reference as if recited in full herein. The analyzer 22 includes a spectrometer and sample handler system.

The system 10 can include a LP-X analysis module and/or circuit 20 that can be onboard the analyzer 22 or at least partially remote from the analyzer 22. If the latter, the analysis module or circuit 20 can reside totally or partially on a server 150. The server 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer. In cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a patient, clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increased risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

Figure 8:
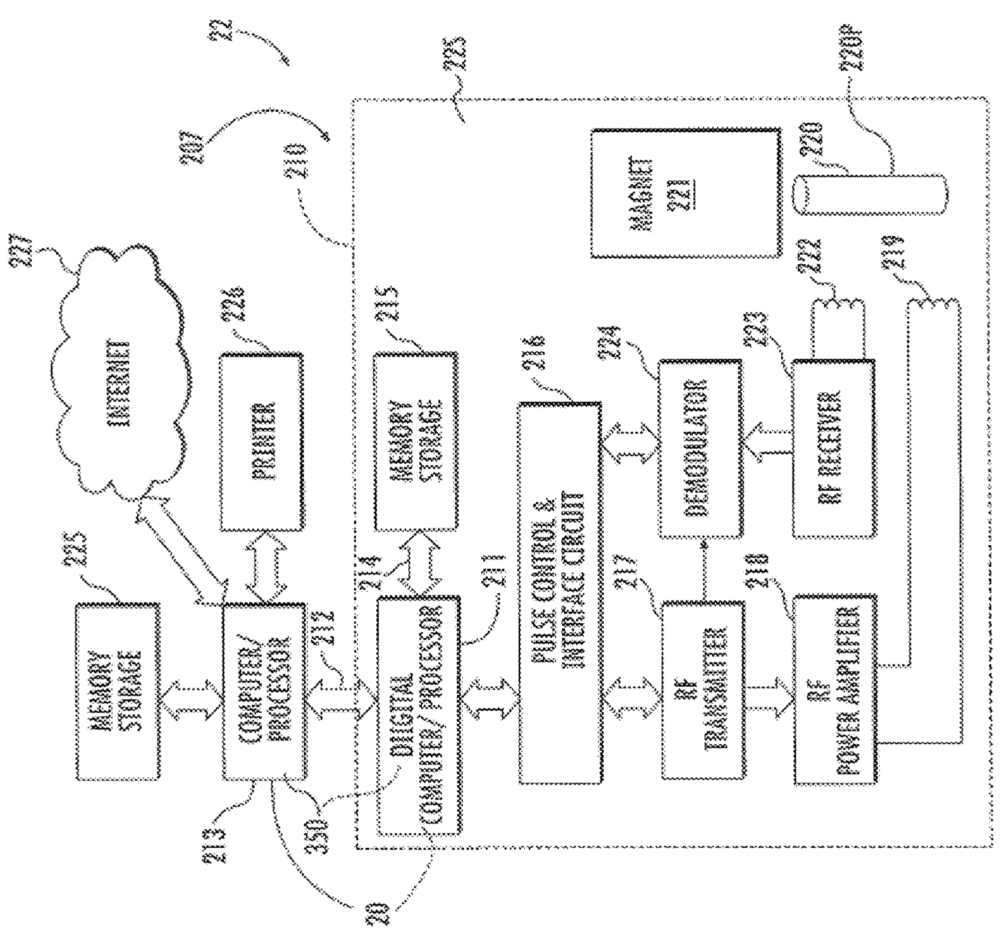
FIG. 8 shows a schematic illustration of a NMR spectroscopy apparatus according to embodiments of the present invention.

FIG. 8 shows an example of the detection of LP-X using NMR. Referring now to FIG. 8, a system 207 for acquiring and calculating the lineshape of a selected sample is illustrated. The system 207 includes an NMR spectrometer 22 *s* for taking NMR measurements of a sample. In one embodiment, the spectrometer 22 is configured so that the NMR measurements are conducted at 400 MHz for proton signals; in other embodiments the measurements may be carried out at between 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/−0.5° C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer 22*s*. These elements include an RF transmitter 217 which produces an RF excitation pulse of the duration, frequency and magnitude directed by at least one digital signal processor that can be onboard or in communication with the digital computer 211, and an RF power amplifier 218 which amplifies the pulse and couples it to the RE transmit coil 219 that surrounds sample cell 220 and/or flow probe 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The lipoprotein measurement and/or LP-X analyzer circuit 20 and/or module 350 FIGS. 8 and 9, can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory or accessible by the computer 213, the computer 213, which may be a laptop computer, desktop computer, workstation computer, electronic notepad, electronic tablet, smartphone or other device with at least one processor or other computer, processes the chemical shift spectrum in accordance with the teachings of the present invention to generate a report which may be output to a printer 226 or electronically stored and relayed to a desired email address or URI Those skilled in this art will recognize that other output devices, such as a computer display screen, electronic notepad, smartphone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that use LP-X evaluations that may be particularly useful in automated screening tests of clinical disease states and/or risk assessment evaluations for screening of in vitro biosamples.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 9:
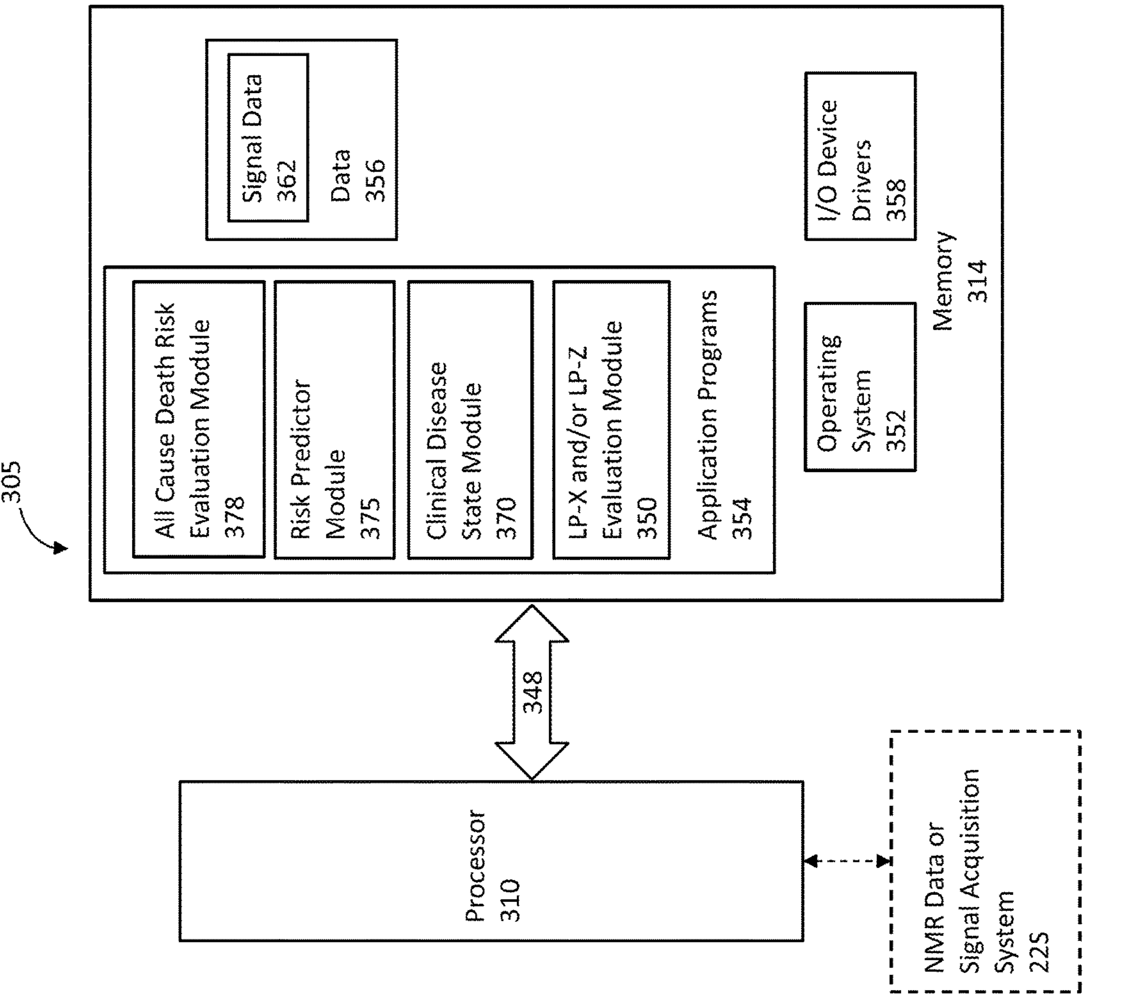
FIG. 9 shows schematic diagram of a data processing system according to embodiments of the present invention.

FIG. 9, is a block diagram of exemplary embodiments of data processing systems 305 that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 9, the memory, 314 may include several categories of software and data used in the data processing system 305: the operating system 352; the application programs 354; the input/output (I/O) device drivers 358; a LP-X Evaluation Module 350; and the data 356. The LP-X and/or LP-Z Evaluation Module 350 can deconvolve NMR signal to reveal a defined NMR signal peak region in proton NMR spectra of a respective biosample to identify a level of LP-X and/or LP-Z.

The data 356 may include signal (constituent and/or composite spectrum lineshape) data 362 which may be obtained from a data or signal acquisition system 320 (e.g., NMR spectrometer 22 *s* and/or analyzer 22). As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000, WindowsXP, Windows 10 from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 9, as will be appreciated by those of skill in the art, other configurations may also be utilized while still benefiting from the teachings of the present invention. Thus, the present invention should not be construed as limited to the configuration of FIG. 9, which is intended to encompass any configuration capable of carrying out the operations described herein.

In certain embodiments, the Module 350 includes computer program code for providing a level of LP-X which may be used as a marker to assess a clinical disease state or risk and/or to indicate whether therapy intervention is desired and/or track efficacy of a therapy or even an unintended consequence of a therapy.

Examples

The present disclosure elucidates the relationship of LP-X determined by agarose gel electrophoresis and LP-X determined by NMR. As such, the relationship between LP-X as determined by agarose gel electrophoresis and LP-X as determined by NMR was explored for both synthetic preparations of LP-X and for plasma samples from subjects having abnormal lipoproteins.

To evaluate correlation between NMR analysis and electrophoretic analysis on agarose gels, changes in lipoproteins were investigated with either gel electrophoresis or by a proton NMR assay using a Vantera analyzer to detect and quantify LP-X by exploiting the unique spectral shape and position of LP-X's lipid methyl group NMR signals. The samples were analyzed for lipoproteins and LP-X by agarose gel electrophoresis and NMR analysis using a "standard" or modified deconvolution model. Samples analyzed by traditional agarose gel electrophoresis were analyzed in parallel with NMR to determine the viability of the NMR assay. Lipoproteins (VLDL, LDL, HDL) and LP-X were separated from plasma by agarose gel electrophoresis and visualized, respectively, by Sudan Black staining for neutral lipids and filipin staining for free cholesterol. LP-X, which migrates toward the cathode in the opposite direction as lipoproteins, was quantified by densitometry.

Figure 10:
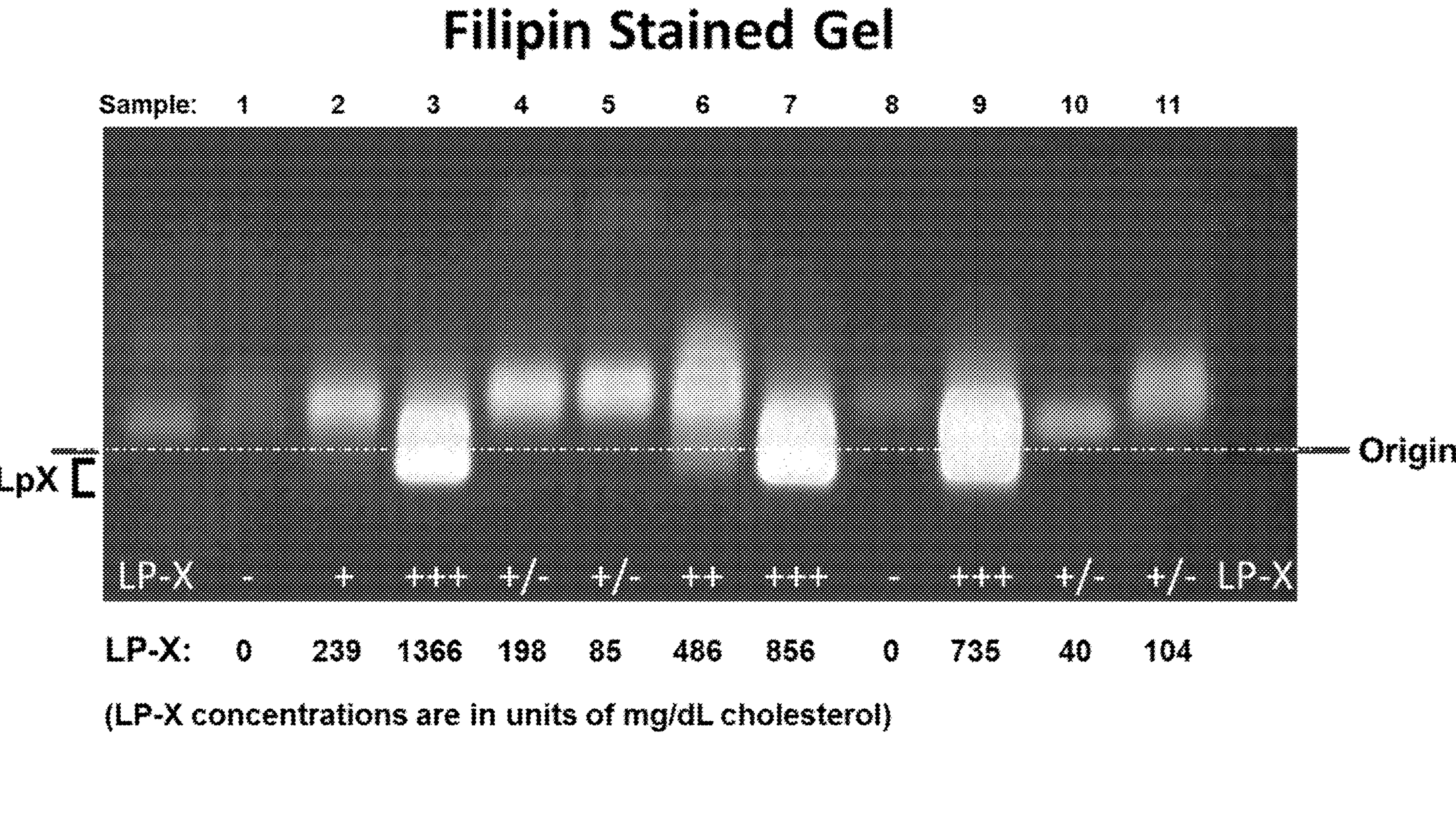
FIG. 10 shows LP-X analysis by agarose gel electrophoresis as compared to values derived from analysis by NMR in accordance with an embodiment of the disclosure.

FIG. 10 shows an agarose gel analysis of LP-X as compared to quantitative values obtained after deconvolving the NMR spectrum obtained for the same set of samples. On the agarose gel the LP-X migrates in the opposite direction from other lipoproteins. Thus the staining above the line of origin represents lipoproteins other than LP-X, while the staining below the origin is LP-X. Quantification of LP-X by NMR using a modified deconvolution model comprising LP-X, LP-Y, and LP-Z yielded the values shown below the gel in FIG. 10, in good agreement with the amounts of LP-X that are visible in the stained gel.

Figure 11:
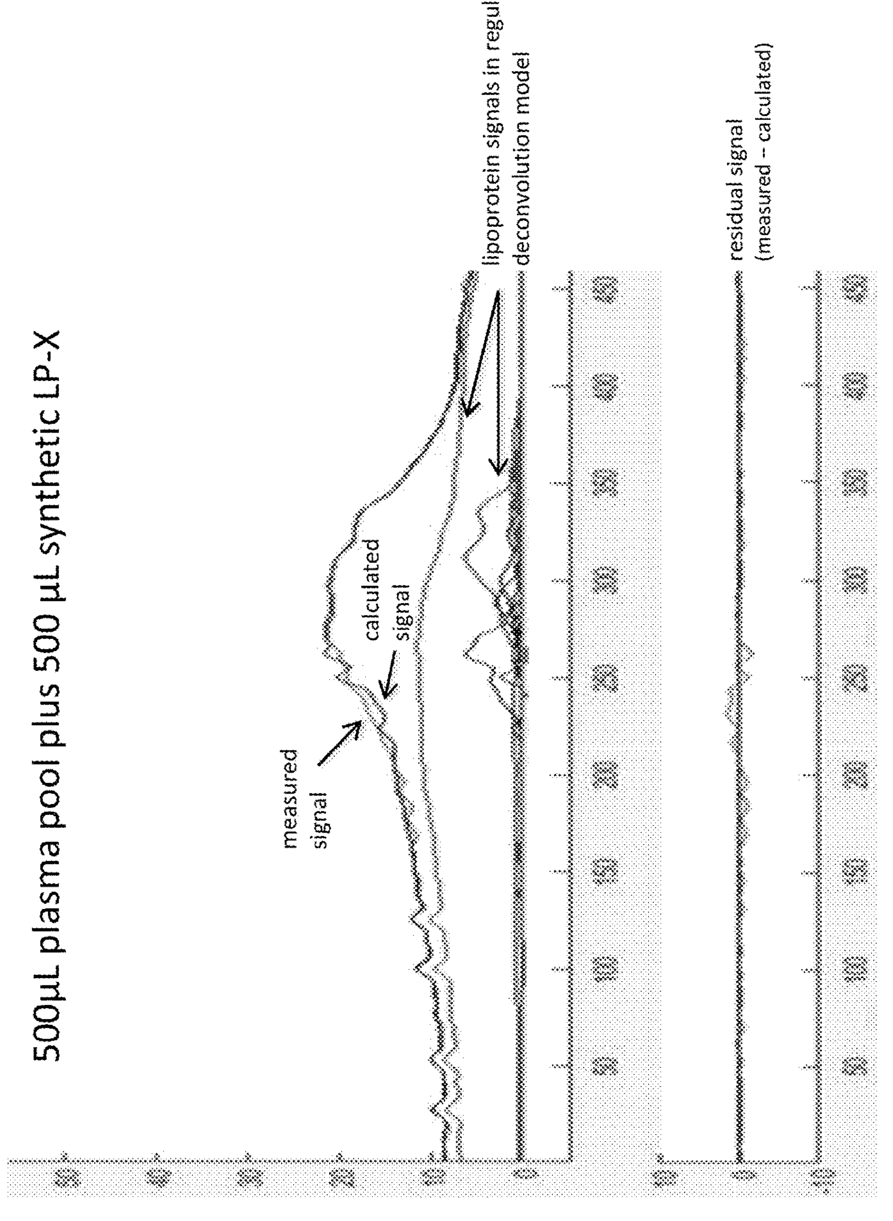
FIG. 11 shows the results of analysis of a plasma sample spiked with artificial (i.e., synthetic) LP-X, when using a regular deconvolution model that does not account for signal from LP-X.

FIG. 11 shows the methyl signal region of the NMR spectrum of a biosample spiked with artificial (i.e., synthetic) LP-X. A normal plasma sample was spiked with synthetically prepared LP-X, and an NMR spectrum of the sample was obtained and analyzed using a standard deconvolution model that does not account for signal from LP-X.

Figure 12:
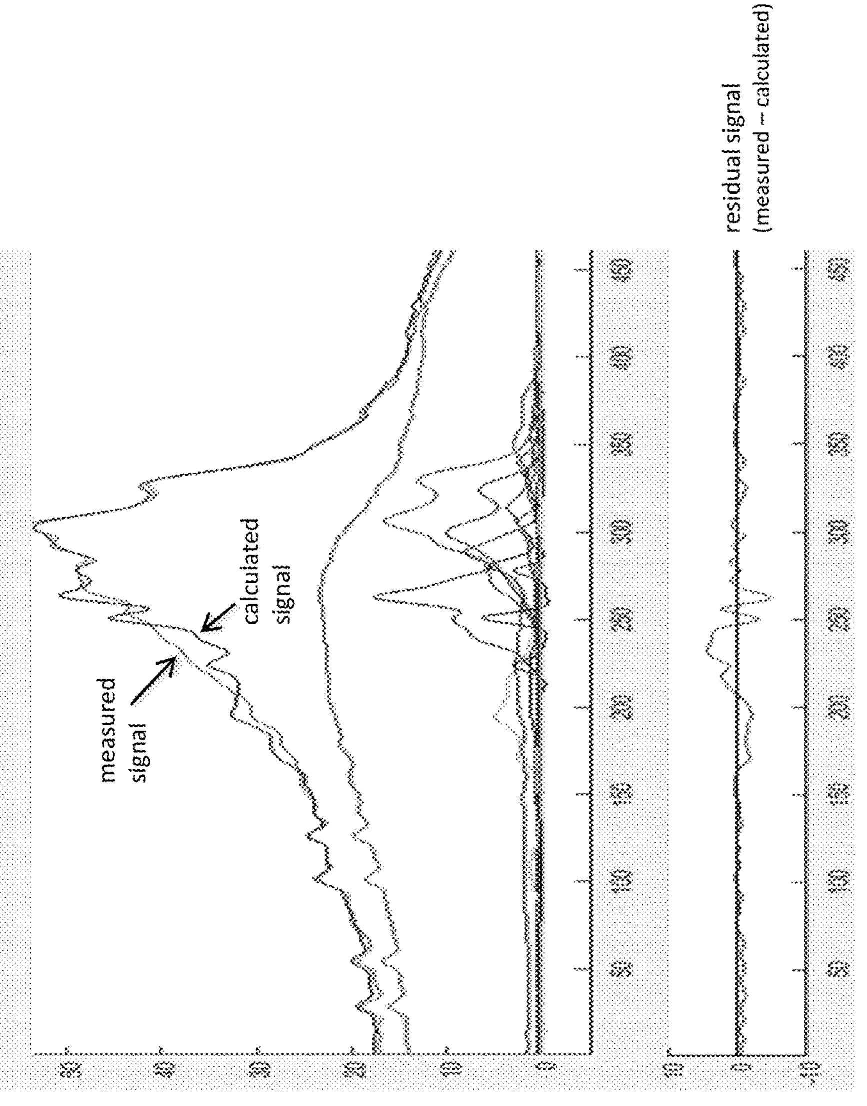
FIG. 12 shows the results of analysis of a plasma sample from a patient with a high level of bilirubin, when using a regular deconvolution model that does not account for signal from LP-X.

FIG. 12 shows the methyl signal region of the NMR spectrum of a biosample from a patient with a high level of bilirubin. A plasma sample from a patient having high bilirubin (i.e., obstructive jaundice) was analyzed. An NMR spectrum of the sample was obtained when using a standard deconvolution model that does not account for signal from LP-X.

Figure 13:
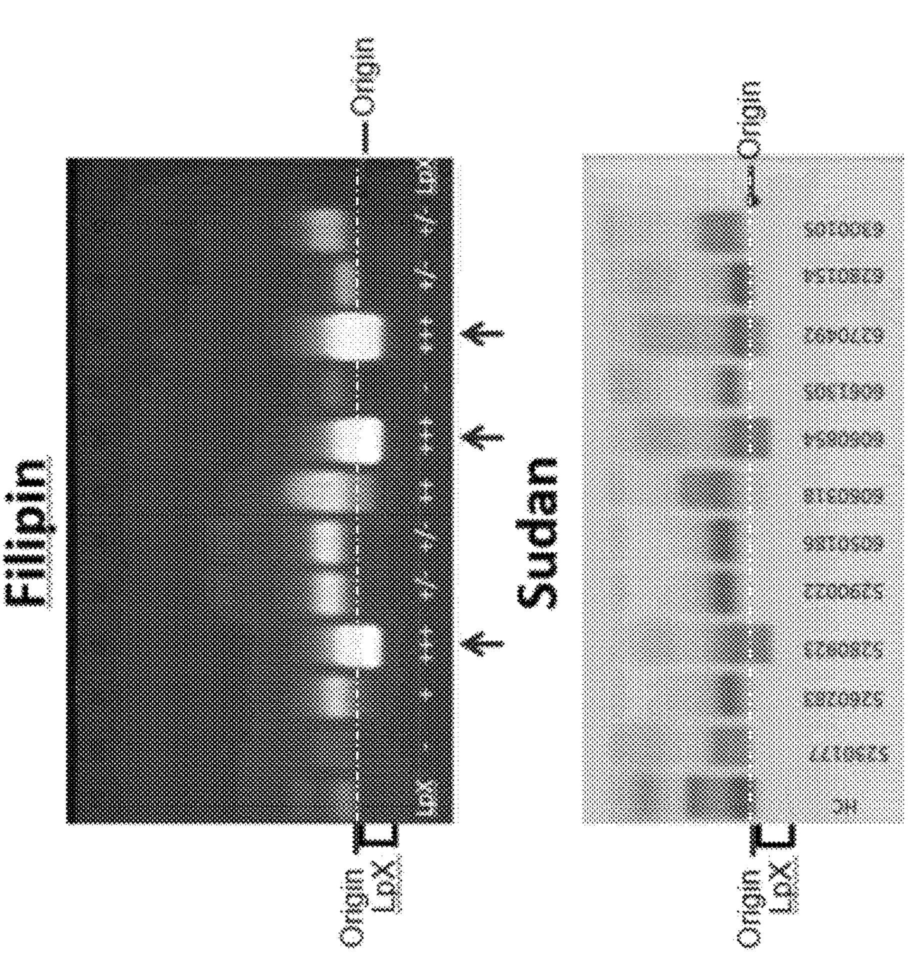
FIG. 13 shows results of agarose gel electrophoresis analysis of samples from patients with high bilirubin.

FIG. 13 shows analysis of samples from high bilirubin patients by agarose gel electrophoresis. Again, LP-X migrates in the opposite direction from the origin with respect to other lipoproteins present in the sample. Thus staining (either Filipin, upper panel, or Sudan, lower panel) demonstrates LP-X below the line of origin, while other lipoproteins are visible above the line of origin. Arrows below the Filipin-stained gel indicate samples with very high (+++) levels of LP-X.

Figure 14:
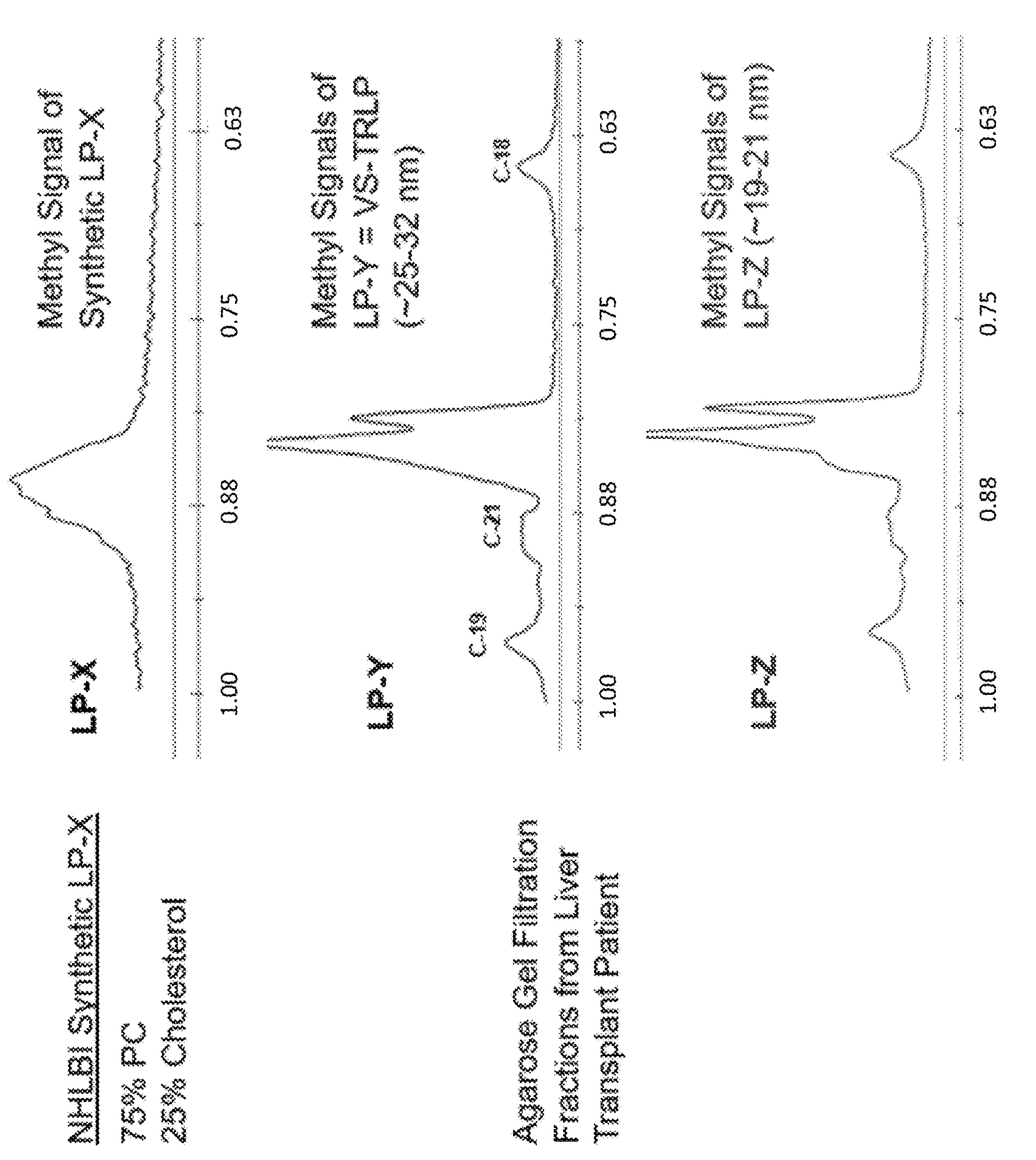
FIG. 14 shows methyl lineshapes of synthetic LP-X (top) and LP-Y and LP-Z isolated by agarose gel filtration chromatography from the plasma of a liver transplant patient.

FIG. 14 shows methyl lineshapes for LP-X, LP-Y, and LP-Z. The LP-X methyl signal was obtained by NMR analysis of a synthetic LP-X preparation. The LP-Y and LP-Z methyl signals were derived from agarose gel filtration fractions isolated from the sample of a liver transplant patient.

Figure 15:
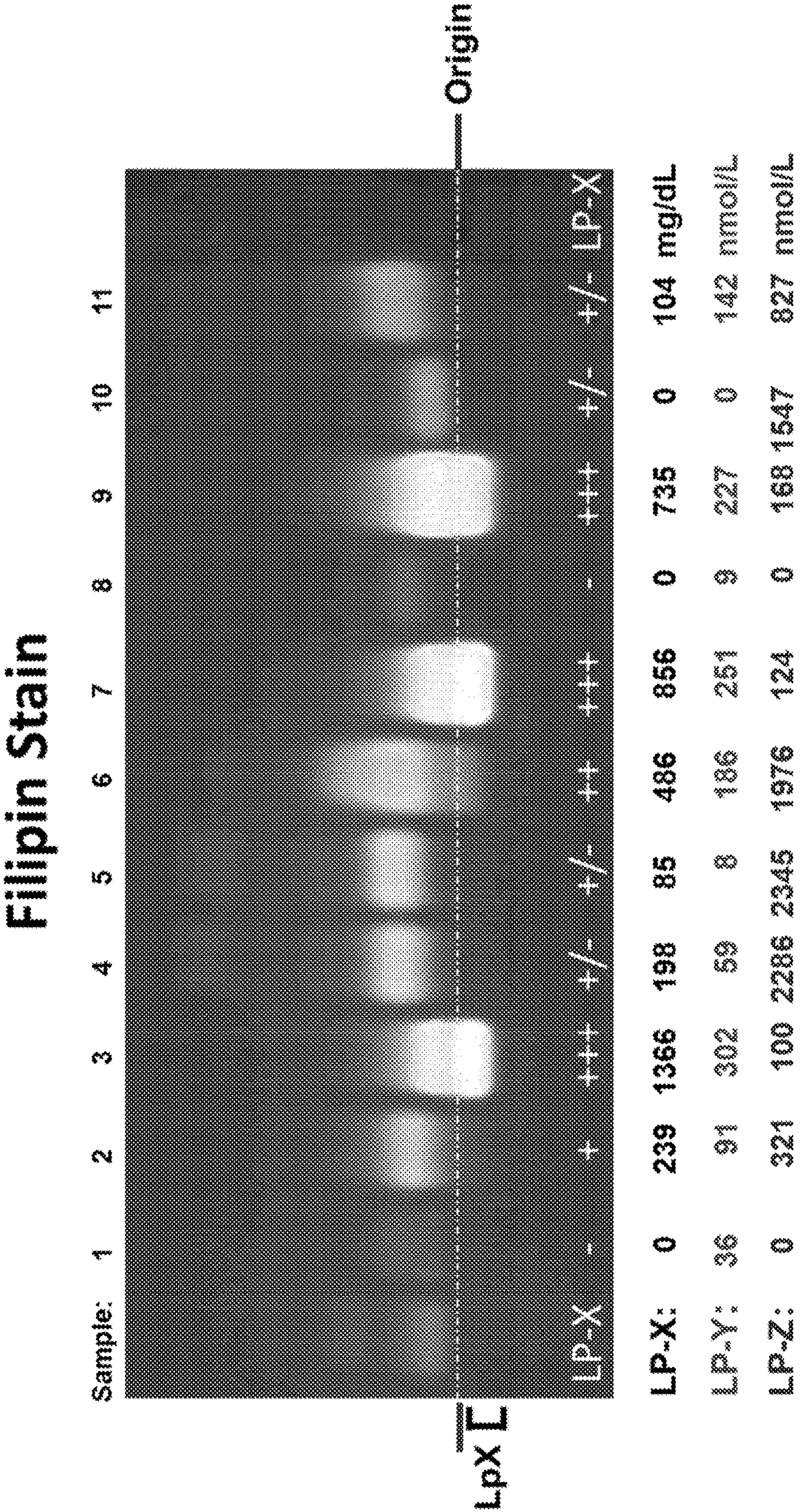
FIG. 15 shows LP-X levels plus LP-Y and LP-Z levels derived from NMR analysis in accordance with an embodiment of the disclosure for the samples of high bilirubin patients analyzed by agarose gel electrophoresis.

FIG. 15 shows a comparison similar to that shown in FIG. 10 described above, except that all three species (LP-X, LP-Y, and LP-Z) were quantified by NMR analysis. Biosamples from patients having high bilirubin were analyzed on agarose gel and compared to quantitative values obtained after deconvolving the NMR spectrum obtained for the same set of samples. On the agarose gel the LP-X migrates in the opposite direction from other lipoproteins. Thus the staining above the line of origin represents lipoproteins other than LP-X, while the staining below the origin is LP-X. Quantification of LP-X, LP-Y, and LP-Z by NMR using a modified deconvolution model comprising LP-X, LP-Y, and LP-Z yielded the values shown below the gel in FIG. 15, in good agreement with the amounts of LP-X that are visible in the stained gel below the line of origin (LP-Z and LP-Y are not uniquely identifiable by agarose electrophoresis). Thus the comparison demonstrates good correlation between quantification demonstrated by agarose gel and NMR assays for LP-X.

Figure 16:
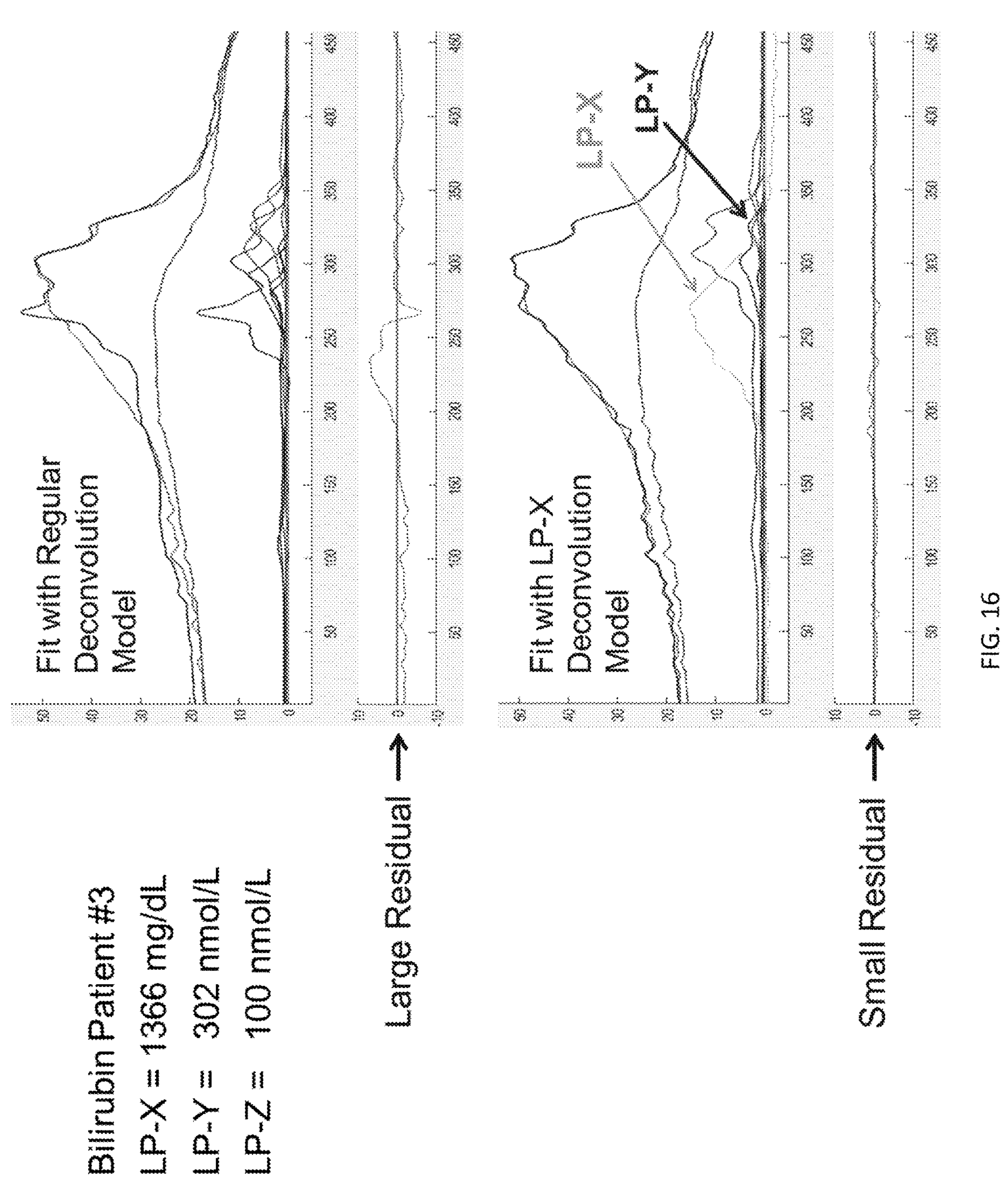
FIG. 16 shows the poor fit and large residual signal (upper) and good fit and small residual signal (lower) resulting from analysis of plasma from a patient (#3) with high bilirubin when using (upper) the regular deconvolution model and (lower) the LP-X deconvolution model that includes reference signals for LP-X, LP-Y, and LP-Z.

FIG. 16 shows a comparison between results using the different analytical methods for a single high bilirubin patient sample. The upper right panel demonstrates a poor fit using NMR analysis with a standard deconvolution model without LP-X and LP-Z, while the lower right panel demonstrates a good fit using a modified deconvolution model that accounts additionally for LP-X and LP-Z.

Figure 17:
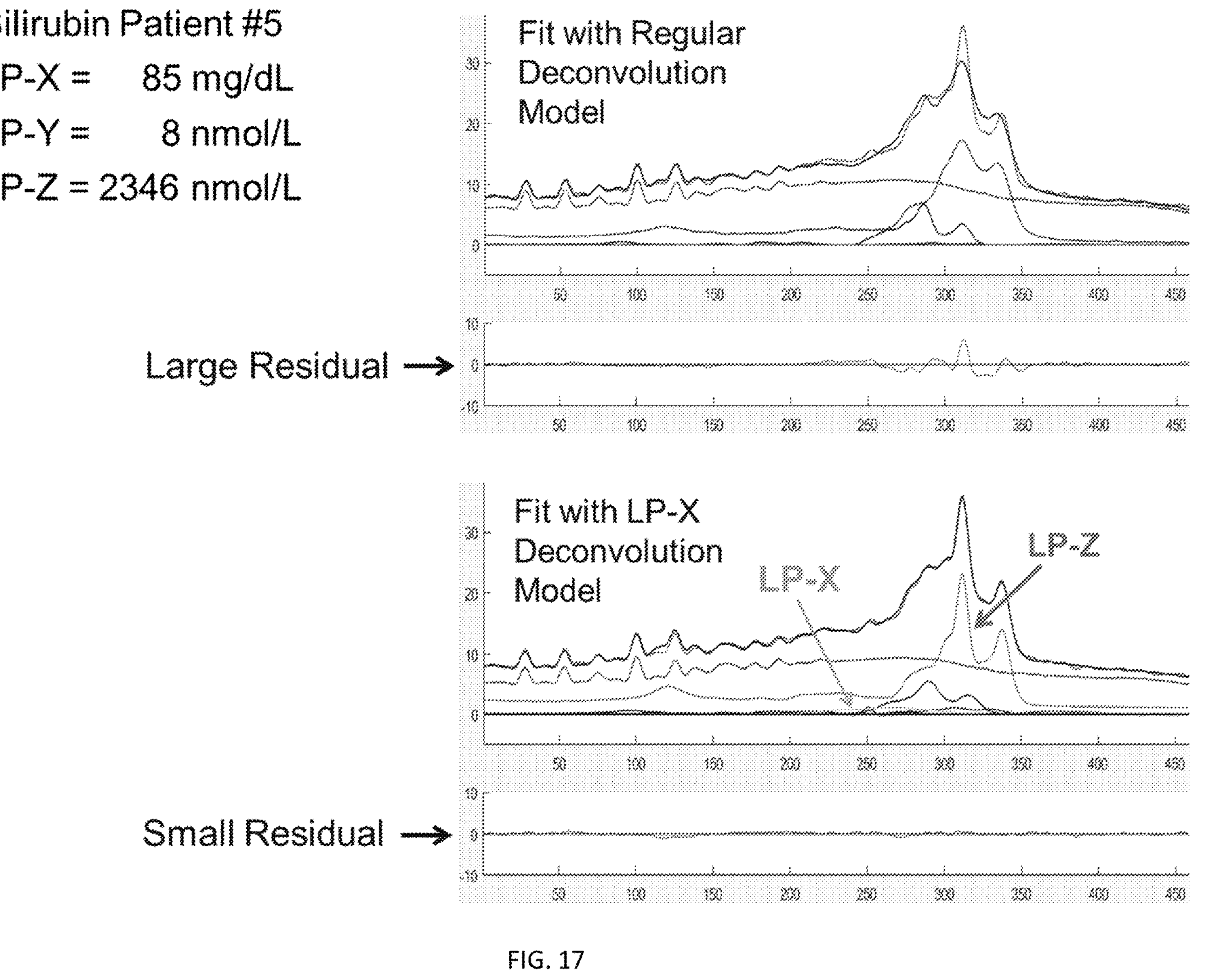
FIG. 17 shows the poor fit and large residual signal (upper) and good fit and small residual signal (lower) resulting from analysis of plasma from another patient (#5) with high bilirubin when using (upper) the regular deconvolution model and (lower) the LP-X deconvolution model that includes reference signals for LP-X, LP-Y, and LP-Z.

FIG. 17 shows a comparison similar to that in FIG. 16, but for a different patient (#5) having high bilirubin. In this example, the patient sample does not have such elevated levels of LP-X as the patient sample of FIG. 16, but instead has elevated LP-Z. Again, the upper right panel demonstrates a poor fit using NMR analysis with a standard deconvolution model without LP-X and LP-Z, while the lower right panel demonstrates a good fit using a modified deconvolution model that accounts additionally for LP-X and LP-Z. The spectral signature of LP-Z is particularly prominent.

Figure 18:
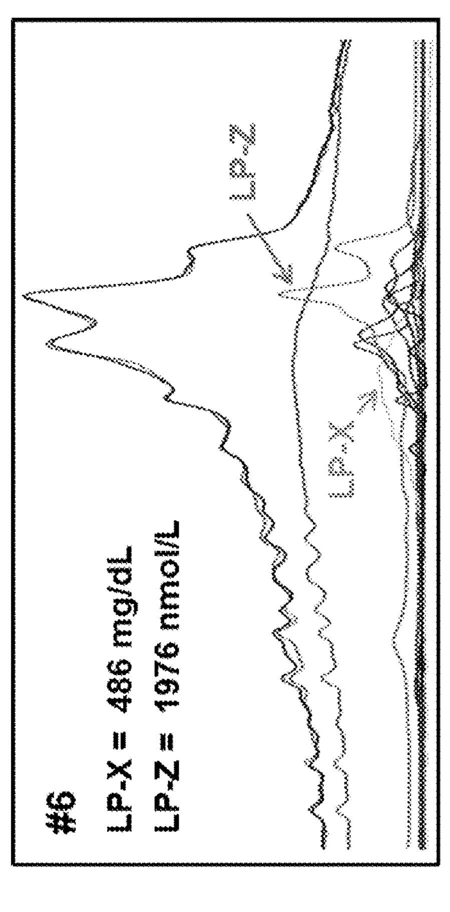
FIG. 18 shows NMR analysis of four different samples having varying levels of LP-X and LP-Z.
Figure 18:
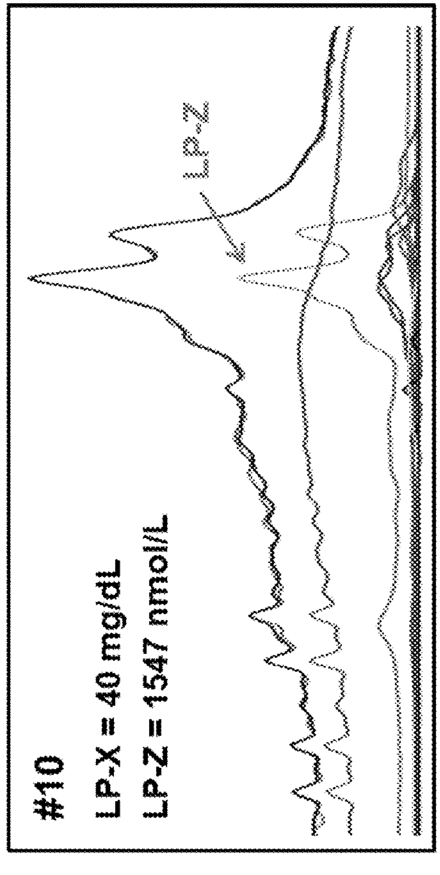
Figure 18:
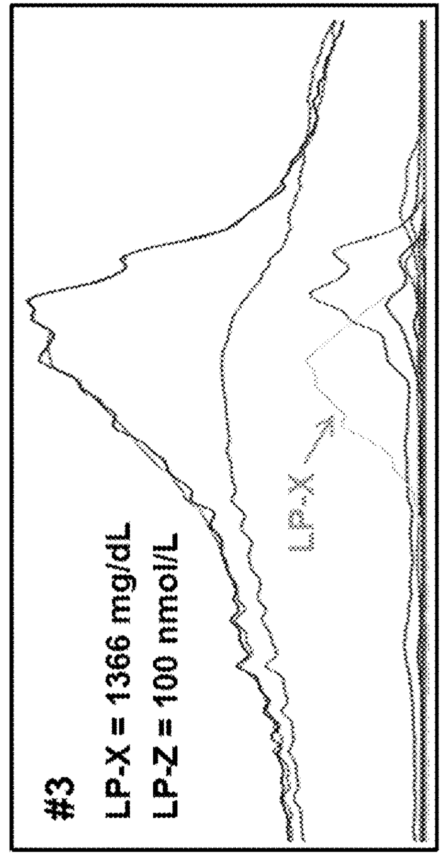
Figure 18:
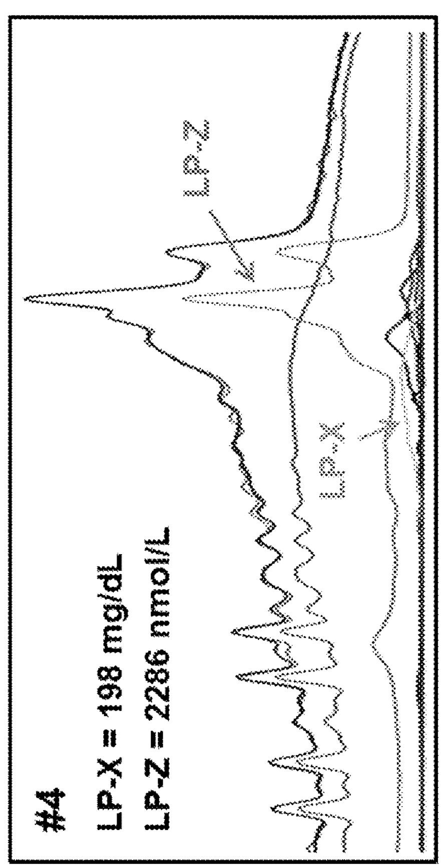

FIG. 18 shows NMR analysis, using a modified deconvolution model that comprises LP-X, LP-Y, and LP-Z, of four different samples having varying levels of LP-X and LP-Z. The spectral fingerprints of LP-X and LP-Z are visible and accurately represent the quantities of those species present in each of the four samples.

Thus, as demonstrated in FIGS. 10-18, using a deconvolution model typical of normal lipoprotein distributions provides a "good fit" for normal subjects, but a "bad fit" for patients having elevated LP-X. This bad fit is due to the contribution of elevated LP-X and in some cases also LP-Y and LP-Z. These samples are abnormal as LP-X and LP-Z have unique spectral shape (lineshape) and these unusual lineshapes of LP-X and LP-Z lipid methyl NMR signals (separately seen in FIG. 14) are not accounted for in the standard model, resulting in a delta between the measured plasma signal and calculated plasma signal for a patient with LP-X and LP-Z present.

Illustrative Embodiments of Suitable Methods, Systems, Computer Programs.

As used below, any reference to methods, systems, or computer programs is to understood as a reference to each of the those methods, systems, or computer programs disjunctively (e.g., "Illustrative embodiments 1-4 is to be understood as illustrative embodiment 1, 2, 3, or 4").

Illustrative embodiment 1 is a method of diagnosing a subject for the presence of LP-X, comprising the steps of acquiring an NMR spectrum of a blood plasma or serum sample obtained from the subject; and programmatically determining the presence of at least one of LP-X or LP-Z in the sample based on the NMR spectrum of the sample, wherein the determining comprises application of a first deconvolution model that includes lipoproteins that are present in a typical human sample but excludes LP-X and LP-Z, and application of a second modified deconvolution model that includes lipoproteins that are present in a typical human sample and further includes LP-X or LP-Z.

Illustrative embodiment 2 is the method of any preceding or subsequent illustrative embodiment, further comprising: (a) producing a measured lipid signal lineshape for an NMR spectrum of a blood plasma or serum sample obtained from a subject; and (b) generating a calculated lineshape for the sample, wherein the calculated lineshape is based on derived concentrations of lipoprotein components potentially present in the sample, wherein lipoprotein components include LP-X and optionally LP-Y and LP-Z, wherein the derived concentration of each of the lipoprotein components is a function of a reference spectrum for that component and a calculated reference coefficient, wherein three of the lipoprotein components for which a concentration is calculated are LP-X, and optionally LP-Y, and LP-Z.

Illustrative embodiment 3 is the method of any preceding or subsequent illustrative embodiment, further comprising: determining the degree of correlation between the initial calculated lineshape of the sample, based on the second deconvolution model, and the measured lineshape of the sample; and determining the presence of LP-X or LP-Z based on a mismatch between the calculated lineshape and the measured lineshape, if the quantification of the residual between the calculated lineshape and the measured lineshape of the sample is above or below a predetermined threshold value.

Illustrative embodiment 4 is the method of any preceding or subsequent illustrative embodiment, wherein one or more of the determining steps comprises calculating the reference coefficients for the calculated lineshape based on a linear least squares fit technique.

Illustrative embodiment 5 is the method of any preceding or subsequent illustrative embodiment, wherein the deconvolution of the NMR spectrum of the sample includes LP-X methyl proton signal at a first region, LP-Y methyl proton signal at a second region, and LP-Z methyl proton signal in a third region.

Illustrative embodiment 6 is the method of any preceding or subsequent illustrative embodiment, wherein the first region is centered at 0.97±0.01 ppm, the second region is centered at 0.78 ppm±0.01 ppm, and the third region is centered at 0.77±0.01 ppm.

Illustrative embodiment 7 is the method of any preceding or subsequent illustrative embodiment, wherein the deconvolution of the NMR spectrum further includes spectra for one or more lipoproteins of LDL, HDL, and VLDL.

Illustrative embodiment 8 is the method of any preceding or subsequent illustrative embodiment, further comprising: deconvolving signal data associated with the LP-X, LP-Y, and LP-Z methyl proton signals; and comparing data from the deconvolved signal data with a priori calibration data corresponding to standard samples with known concentrations of LP-X, LP-Y, and LP-Z to determine the concentrations of LP-X or LP-Z in the sample.

Illustrative embodiment 9 is the method of any preceding or subsequent illustrative embodiment, further comprising determining the concentration of LP-Y and/or LP-Z in the sample.

Illustrative embodiment 10 is the method of any preceding or subsequent illustrative embodiment, wherein the sample is a blood, serum, plasma, cerebral spinal fluid, or urine.

Illustrative embodiment 11 is the method of any preceding or subsequent illustrative embodiment, further comprising the step of producing a report listing the concentrations of the lipoprotein constituents present in the sample.

Illustrative embodiment 12 is the method of any preceding or subsequent illustrative embodiment, further comprising the step of identifying a condition associated with elevated abnormal proteins LP-X, LP-Y, or LP-Z in the subject following the determining step.

Illustrative embodiment 13 is a method of evaluating a patient's response to a therapy comprising: obtaining a first biosample from the patient at a first time point; obtaining a second biosample from the patient at a second time point, wherein the first time point is before the second time point; measuring the patient's LP-X concentration in the first and the second biosamples; determining the patient is responsive to the therapy if the concentration of LP-X in the second biosample is lower than the concentration of LP-X in the first biosample, wherein the measuring LP-X is by programmatically determining the presence of LP-X in the sample based on the NMR spectrum of the sample, wherein the NMR spectrum of the sample includes LP-X, LP-Y, and LP-Z.

Illustrative embodiment 14 is a system for screening a subject for the presence of LP-X, comprising: an NMR spectrometer for acquiring a measured lipid signal lineshape of an NMR spectrum of a biosample; a computer program means for storing the measured lineshape of the sample; a computer program means for storing reference spectra for each of a plurality of lipoprotein constituents, wherein one or more of the constituents being LP-X, LP-Y, and LP-Z; a computer program means for calculating a calculated lineshape based on the derived concentrations of the lipoprotein constituents of the biosample and the reference spectra; and a computer program means for comparing the measured lipid signal lineshape and the calculated lineshape to determine the degree of correlation between the calculated lineshape and the measured lipid signal lineshape.

Illustrative embodiment 15 is the system of any preceding or subsequent illustrative embodiment, wherein the computer program means for storing reference spectra comprise means for storing lipoproteins HDL, LDL, and/or VLDL.

Illustrative embodiment 16 is the system of any preceding or subsequent illustrative embodiment, further comprising an output device for producing a report indicating the presence of LP-X and/or the concentration of LP-X.

Illustrative embodiment 17 is a system configured to determine the concentrations of LP-X in patient biosamples, the system comprising: one or more processors configured to: (a) obtain and analyze NMR signal spectra of the biosamples, wherein the NMR signal spectra comprises LP-X methyl proton signal at a first region, LP-Y methyl proton signal at a second region, and LP-Z methyl proton signal at a third region; (b) deconvolve signal data associated with the LP-X, LP-Y, and LP-Z signals; and (c) compare data from the deconvolved signal data with a priori calibration data corresponding to standard samples with known concentrations of LP-X, LP-Y, and LP-Z to determine the concentrations of LP-X or LP-Z in the biosample.

Illustrative embodiment 18 is the system of any preceding or subsequent illustrative embodiment, wherein the first region is centered at 0.97±0.01 ppm, the second region is centered at 0.78 ppm±0.01 ppm, and the third region is centered at 0.77±0.01 ppm.

Illustrative embodiment 19 is a computer program product for determine the concentrations of LP-X in patient biosamples, the computer program product comprising: a non-transitory computer readable storage medium having computer readable program code embodied in the medium, the computer-readable program code comprising: a computer readable program code that obtains NMR signal spectra comprising LP-X methyl proton signal at a first region, LP-Y methyl proton signal at a second region, and LP-Z methyl proton signal at a third region; and a computer readable program code that determines the concentrations of LP-X in the biosample.

Illustrative embodiment 20 is the computer program of any preceding or subsequent illustrative embodiment, wherein the non-transitory computer readable storage medium further comprises computer readable program code for deconvolving signal data associated with the LP-X, LP-Y, and LP-Z signals.

What is claimed is:

1. A method of diagnosing a subject for the presence of LP-X, comprising the steps of:

acquiring an NMR spectrum of a biosample obtained from the subject, wherein the NMR spectrum includes a zone from 0.75 ppm to 1.0 ppm; and programmatically determining the presence of at least one of LP-X or LP-Z in the biosample based on the NMR spectrum of the biosample, wherein the determining comprises application of a first deconvolution model that includes lipoproteins that are present in the zone for a typical human sample but excludes LP-X and LP-Z, and application of a second modified deconvolution model that includes lipoproteins that are present in the zone for a typical human sample and further includes LP-X or LP-Z.

2. The method of claim 1, further comprising:

(a) producing a measured lipid signal lineshape for an NMR spectrum of a biosample obtained from a subject; and (b) generating a calculated lineshape for the biosample, wherein the calculated lineshape is based on derived concentrations of lipoprotein components potentially present in the biosample, wherein lipoprotein components include LP-X and optionally LP-Y and LP-Z, wherein the derived concentration of each of the lipoprotein components is a function of a reference spectrum for that component and a calculated reference coefficient, wherein three of the lipoprotein components for which a concentration is calculated are LP-X, and optionally LP-Y, and LP-Z.

3. The method of claim 2, further comprising:

determining the degree of correlation between the initial calculated lineshape of the biosample, based on the second deconvolution model, and the measured lineshape of the biosample; and determining the presence of LP-X or LP-Z based on a mismatch between the calculated lineshape and the measured lineshape, if the degree of correlation between the calculated lineshape and the measured lineshape of the biosample is above or below a predetermined threshold value.

4. The method of claim 3, wherein one or more of the determining steps comprises calculating the reference coefficients for the calculated lineshape based on a linear least squares fit technique.

5. The method of claim 2, further comprising the step of identifying a condition associated with elevated concentrations of proteins LP-X, LP-Y, or LP-Z in the biosample of the subject.

6. The method of claim 1, wherein the deconvolution of the NMR spectrum of the biosample includes LP-X methyl proton signal at a first region within the zone, LP-Y methyl proton signal at a second region within the zone, and LP-Z methyl proton signal in a third region within the zone.

7. The method of claim 6, further comprising:
deconvolving signal data associated with the LP-X, LP-Y, and LP-Z methyl proton signals; and
comparing data from the deconvolved signal data with a priori calibration data corresponding to standard samples with known concentrations of LP-X, LP-Y, and LP-Z to determine the concentrations of LP-X or LP-Z in the biosample.

8. The method of claim 7, further comprising determining the concentration of LP-Y and/or LP-Z in the biosample.

9. The method of claim 6, wherein the LP-X methyl proton signal is resolved from the LP-Z methyl proton signal within the zone.

10. The method of claim 6, wherein the LP-X methyl proton signal is centered at 0.84 ppm and the LP-Z methyl proton signal is centered at 0.81 ppm.

11. The method of claim 1, further comprising determining the presence of one or more lipoproteins of LDL, HDL, and VLDL based on the NMR spectrum of the biosample.

12. The method of claim 1, wherein the biosample is blood, serum, plasma, cerebral spinal fluid, or urine.

13. The method of claim 1, further comprising the step of producing a report listing the concentrations of the lipoprotein constituents present in the biosample.

14. A system for screening a subject for the presence of LP-X, comprising:
an NMR spectrometer for acquiring a measured lipid signal lineshape of an NMR spectrum of a biosample, wherein the NMR spectrum includes a zone from 0.75 ppm to 1.0 ppm;
a computer program means for storing the measured lineshape of the sample;
a computer program means for storing reference spectra for each of a plurality of lipoprotein constituents, wherein one or more of the constituents being LP-X, LP-Y, and LP-Z;
a computer program means for calculating a calculated lineshape based on the derived concentrations of the lipoprotein constituents of the biosample and the reference spectra; and
a computer program means for comparing the measured lipid signal lineshape and the calculated lineshape to determine the degree of correlation between the calculated lineshape and the measured lipid signal lineshape.

15. The system of claim 14, wherein the computer program means for storing reference spectra comprise means for storing lipoproteins HDL, LDL, and/or VLDL.

16. The system of claim 14, further comprising an output device for producing a report indicating the presence of LP-X and/or the concentration of LP-X.

17. The system of claim 14, wherein the NMR signal spectrum comprises an LP-X methyl proton signal at a first region and an LP-Z methyl proton signal at a third region.

18. A computer program product for determining the concentration of LP-X in patient biosamples, the computer program product comprising:
a non-transitory computer readable storage medium having computer readable program code embodied in the medium, the computer-readable program code comprising:
a computer readable program code that obtains NMR signal spectra that includes a zone from 0.75 ppm to 1.0 ppm, wherein the zone comprises an LP-X methyl proton signal at a first region, an LP-Y methyl proton signal at a second region, and an LP-Z methyl proton signal at a third region; and
a computer readable program code that determines the concentration of LP-X in the biosample.

19. The computer program product of claim 18, wherein the non-transitory computer readable storage medium further comprises computer readable program code for deconvolving signal data associated with the LP-X, LP-Y, and LP-Z signals.

* * * * *